(12) United States Patent
Zhu et al.

(10) Patent No.: US 11,155,626 B2
(45) Date of Patent: Oct. 26, 2021

(54) ANTI-HUMAN PD-L1 HUMANIZED MONOCLONAL ANTIBODY AND APPLICATION THEREOF

(71) Applicant: REYOUNG (SUZHOU) BIOLOGY SCIENCE & TECHNOLOGY CO., LTD, Jiangsu (CN)

(72) Inventors: Yixiang Zhu, Jiangsu (CN); Shuhua Guo, Jiangsu (CN); Jiachun Zhang, Jiangsu (CN); Ge Li, Jiangsu (CN)

(73) Assignee: REYOUNG (SUZHOU) BIOLOGY SCIENCE & TECHNOLOGY CO., LTD, Jiangsu (CN)

( * ) Notice: Subject to any disclaimer, the term of this patent is extended or adjusted under 35 U.S.C. 154(b) by 270 days.

(21) Appl. No.: 16/084,710

(22) PCT Filed: Jun. 3, 2016

(86) PCT No.: PCT/CN2016/084643
§ 371 (c)(1),
(2) Date: Sep. 13, 2018

(87) PCT Pub. No.: WO2017/197667
PCT Pub. Date: Nov. 23, 2017

(65) Prior Publication Data
US 2019/0077867 A1 Mar. 14, 2019

(30) Foreign Application Priority Data
May 20, 2016 (CN) .......................... 201610340678.3

(51) Int. Cl.
| | | |
|---|---|---|
| *C07K 16/28* | (2006.01) | |
| *A61K 39/395* | (2006.01) | |
| *A61P 35/00* | (2006.01) | |
| *C12N 5/12* | (2006.01) | |
| *C12N 15/62* | (2006.01) | |

(52) U.S. Cl.
CPC ........ *C07K 16/2827* (2013.01); *A61K 39/395* (2013.01); *A61P 35/00* (2018.01); *C07K 16/28* (2013.01); *C12N 5/12* (2013.01); *C12N 15/62* (2013.01); *C07K 2317/24* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| 8,552,154 | B2 * | 10/2013 | Freeman ............ | C07K 16/2827 530/387.1 |
|---|---|---|---|---|
| 2014/0044738 | A1 * | 2/2014 | Langermann ...... | A61K 39/3955 424/172.1 |
| 2014/0328862 | A1 * | 11/2014 | Scheid ................ | A61P 31/12 424/160.1 |
| 2015/0274835 | A1 | 10/2015 | Marasco et al. | |
| 2016/0108123 | A1 | 4/2016 | Freeman et al. | |

FOREIGN PATENT DOCUMENTS

| CN | 1753912 | A | 3/2006 |
|---|---|---|---|
| CN | 101213297 | A | 7/2008 |
| CN | 102131828 | A | 7/2011 |
| CN | 104250302 | A | 12/2014 |
| CN | 105175544 | A | 12/2015 |
| WO | 2011110604 | A1 | 9/2011 |
| WO | 2015035606 | A1 | 3/2015 |
| WO | 2015085847 | A1 | 6/2015 |
| WO | 2016022630 | A1 | 2/2016 |

OTHER PUBLICATIONS

Damschroder et al. Molecular Immunology (2004) 41: 985-1000.*
Khan et al. Sci. Rep. (2017) 7, 45163; doi: 10.1038/srep45163 (12 pages).*
Zhu et al. Cell (2015) 161: 1280-1292.*
Lee et al. Nature Medicine (2016) 22: 1456-1464.*
Abdiche et al. mAbs (2016) 8: 264-277.*
Konitzer et al. mAbs (2017) 9: 536-549.*
Ferrara et al. mAbs (2015) 7: 32-41.*
Parola et al. Immunology (2018) 153:31-41.*
Boyd et al. Current Opinion in Immunology 2016, 40: 103-109.*
Van Regenmortel MHV. Front. Immunol. (2018) vol. 8, Article 2009 (11 pages).*
Conroy et al. Methods (2017) 116: 12-22.*
Sheehan et al. Microbiol. Spectr. (2015) 3(1): AID-0028-2014; 17 pages.*
Chothia C, Lesk A M, Tramontano A, et al. Conformations of immunoglobulin hypervariable regions[J]. Nature, 1989, 342(6252):877-883.
Chothia C, Lesk A M. Canonical structures for the hypervariable regions of immunoglobulins.[J]. Journal of Molecular Biology, 1987, 196(4):901-917.
International Search Report & Written Opinion dated Feb. 14, 2017 from PCT Application No. PCT/CN2016/084643.
International Search Report & Written Opinion from PCT Application No. PCT/CN2016/084644.

* cited by examiner

*Primary Examiner* — Ilia I Ouspenski
(74) *Attorney, Agent, or Firm* — Innovation Capital Law Group, LLP; Vic Lin

(57) ABSTRACT

The present invention relates to the biomedicine field, in particular to an anti-human PD-L1 humanized monoclonal antibody and its applications. The invention obtains an anti-human PD-L1 humanized monoclonal antibody with good specificity, high affinity and stability by screening, and the antibody can specifically bind to human PD-L1 instead of binding to members of B7 family, and it can bind to active T-cells to strengthen the activation of T-cells, so it can significantly inhibit the growth of tumor.

14 Claims, 7 Drawing Sheets
Specification includes a Sequence Listing.

SEQUENCE LISTING

<160> NUMBER OF SEQ ID NOS: 56

<210> SEQ ID NO 1
<211> LENGTH: 363
<212> TYPE: DNA
<213> ORGANISM: Artificial Sequence
<220> FEATURE:
<223> OTHER INFORMATION: Synthesized

<400> SEQUENCE: 1

```
aaggtccagc tgcagcagtc tggagctgag ctggtgaaac ccggggcatc agtgaagctg    60
tcctgcaagg cttctggcta caccttcact aaatatatta tacactggat aaagcagagg   120
tctggacagg gtcttgagtg gattgggtgg ttttaccctg gaagtggtaa tatcaggtac   180
aatgagaaaa tcaagggcaa ggccacattg actgcggaca atcctccag cacagtctat    240 atggagctta gtggattgac atctgaggac tctgcggtct atttctgtgc aagacacggg   300
gaactgggag gcggttactt ctttgactac tggggccaag gcaccactct cacggtctcc   360
tca                                                                 363
```

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

```
Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Ser Asn Ile
            20                  25                  30

His Trp Tyr Gln Gln Lys Thr Gly Ser Ser Pro Lys Pro Trp Ile Tyr
        35                  40                  45

Ala Thr Ser Asn Leu Ala Ser Gly Ala Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Pro Gly Thr Lys Leu Glu Leu Lys Arg
            100                 105
```

<210> SEQ ID NO 3
<211> LENGTH: 321
<212> TYPE: DNA
<213> ORGANISM: Artificial Sequence
<220> FEATURE:
<223> OTHER INFORMATION: Synthesized

<400> SEQUENCE: 3

```
caaattgttc tctcccagtc tccaacaatc ctgtctgcat ctccagggga gaaggtcaca    60
atgacttgca gggccagctc cagtgtaagt aacatacact ggtaccagca gaagacagga   120
tcctccccca aaccctggat ttatgccaca tccaacctgg cttctggagc ccctgttcgc   180
ttcagtggca gtgggtctgg gacctcttat tctctcacaa tcagcagagt ggaggctgaa   240
gatgctgcca cttattactg ccagcagtgg agtagtaacc cactcacgtt cggtcctggg   300
accaagctgg agctgaaacg g                                             321
```

<210> SEQ ID NO 4
<211> LENGTH: 121
<212> TYPE: PRT
<213> ORGANISM: Artificial Sequence
<220> FEATURE:
<223> OTHER INFORMATION: Synthesized

<400> SEQUENCE: 4

Lys Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Lys Tyr
            20                  25                  30

Ile Ile His Trp Ile Lys Gln Arg Ser Gly Gln Gly Leu Glu Trp Ile
            35                  40                  45

Gly Trp Phe Tyr Pro Gly Ser Gly Asn Ile Arg Tyr Asn Glu Lys Ile
        50                  55                  60

Lys Gly Lys Ala Thr Leu Thr Ala Asp Lys Ser Ser Thr Val Tyr
65                  70                  75                  80

Met Glu Leu Ser Gly Leu Thr Ser Glu Asp Ser Ala Val Tyr Phe Cys
                85                  90                  95

Ala Arg His Gly Glu Leu Gly Gly Tyr Phe Phe Asp Tyr Trp Gly
            100                 105                 110

Gln Gly Thr Thr Leu Thr Val Ser Ser
            115                 120

<210> SEQ ID NO 5
<211> LENGTH: 363
<212> TYPE: DNA
<213> ORGANISM: Artificial Sequence
<220> FEATURE:
<223> OTHER INFORMATION: Synthesized

<400> SEQUENCE: 5
gaggtgcagc tggtgcagag cggcgccgag gtgaagaaac ctggcgcctc cgtgaaggtg    60
agctgcaagg cctccggcta caccttcacc aagtacatca tccactgggt gcggcaagcc   120
cctggacagg gactggaatg gatgggctgg ttctaccctg gttctggcaa catccggtac   180
aacgagaaga tcaagggcag ggtgaccatg acccgggaca ccagcacctc caccgtgtac   240
atggagctgt cctccctgag gagcgaggac accgccgtgt attactgcgc taggcacgga   300
gagctgggcg gaggctactt cttcgactac tggggccagg gcacaaccgt gaccgtgtcc   360
tcc                                                                 363

<210> SEQ ID NO 6
<211> LENGTH: 121
<212> TYPE: PRT
<213> ORGANISM: Artificial Sequence
<220> FEATURE:
<223> OTHER INFORMATION: Synthesized

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
            20                  25                  30

Ile Ile His Trp Val Arg Gln Ala Pro Gly Gln Gly Leu Glu Trp Met
            35                  40                  45

Gly Trp Phe Tyr Pro Gly Ser Gly Asn Ile Arg Tyr Asn Glu Lys Ile
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Glu Leu Gly Gly Tyr Phe Phe Asp Tyr Trp Gly
            100                 105                 110

```
Gln Gly Thr Thr Val Thr Val Ser Ser
        115                 120
```

<210> SEQ ID NO 7
<211> LENGTH: 321
<212> TYPE: DNA
<213> ORGANISM: Artificial Sequence
<220> FEATURE:
<223> OTHER INFORMATION: Synthesized

<400> SEQUENCE: 7

| | | | | | |
|---|---|---|---|---|---|
| gatatccagc | tgacccagag | cccctccttt | ctgtccgcct | ccgtgggcga | cagggtgacc | 60 |
| atcacctgca | gggccagctc | cagcgtgagc | aacatccact | ggtatcaaca | gaagcctggc | 120 |
| aaggccccca | agccctggat | ctacgccacc | tccaacctgg | ccagcggcgt | gcctagcagg | 180 |
| ttcagcggtt | ctggctccgg | caccgagttc | accctgacca | tctcctccct | gcagcccgag | 240 |
| gacttcgcca | cctactactg | ccagcagtgg | tccagcaacc | ccctgacctt | tggccagggc | 300 |
| accaagctgg | agatcaagag | g | | | | 321 |

<210> SEQ ID NO 8
<211> LENGTH: 107
<212> TYPE: PRT
<213> ORGANISM: Artificial Sequence
<220> FEATURE:
<223> OTHER INFORMATION: Synthesized

<400> SEQUENCE: 8

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Asn Ile
            20                  25                  30

His Trp Tyr Gln Gln Lys Pro Gly Lys Ala Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105
```

<210> SEQ ID NO 9
<211> LENGTH: 1359
<212> TYPE: DNA
<213> ORGANISM: Artificial Sequence
<220> FEATURE:
<223> OTHER INFORMATION: Synthesized

<400> SEQUENCE: 9

| | | | | | |
|---|---|---|---|---|---|
| gaggtgcagc | tggtgcagag | cggcgccgag | gtgaagaaac | tggcgcctc | cgtgaaggtg | 60 |
| agctgcaagg | cctccggcta | caccttcacc | aagtacatca | tccactgggt | gcggcaagcc | 120 |
| cctggacagg | gactggaatg | gatgggctgg | ttctaccctg | gttctggcaa | catccggtac | 180 |
| aacgagaaga | tcaagggcag | ggtgaccatg | acccgggaca | ccagcacctc | caccgtgtac | 240 |
| atggagctgt | cctccctgag | gagcgaggac | accgccgtgt | attactgcgc | taggcacgga | 300 |
| gagctgggcg | gaggctactt | cttcgactac | tggggccagg | gcacaaccgt | gaccgtgtcc | 360 |
| tccgccagca | ccaagggacc | atccgtgttc | ccactggctc | caagctctaa | atccactagc | 420 |

```
ggaggcaccg cagccctggg atgtctggtg aaggattact cccagagcc cgtcacagtg      480 tcatggaact ccggggctct gacctctggt gtccacacat ttccagcagt gctgcagagt      540
tcaggcctgt actccctgtc cagcgtggtc acagtgccct ctagttcact gggaactcag      600
acctatatct gcaacgtgaa tcacaagcca tccaatacta agtcgacaa gaaagtggag       660 cccaagagct gtgataaaac acatacttgc cccccttgtc ctgcaccaga actgctggga      720
ggaccatccg tgttcctgtt tccacccaag cctaaagaca ctctgatgat ttctcgaaca      780
cccgaggtca cttgcgtggt cgtggacgtg tcccacgagg atcctgaagt caagtttaac      840
tggtacgtgg atggagtcga agtgcataat gctaagacaa aacctagaga ggaacagtac      900
gccagtacat atagagtcgt gtcagtcctg actgtgctgc atcaggactg gctgaacggg      960
aaggagtata agtgcaaagt gtccaataag gctctgcccg cacctatcga gaaaactatt     1020
agcaaggcta aaggccagcc tagggaacca caggtgtaca ccctgcctcc atctcgggag     1080
gaaatgacta gaaccaggt cagtctgacc tgtctggtga aaggcttcta tccttccgac      1140
atcgcagtgg agtgggaaag caatggacag ccagagaaca attacaagac cacccccct     1200 gtgctggaca gcgatgggtc tttctttctg tatagtaagc tgaccgtgga taaatcacgg     1260
tggcagcagg gtaatgtctt ttcttgtagt gtgatgcacg aagccctgca caaccattac     1320
actcagaaat ccctgtcact gtcccctgga aagtgataa                            1359
```

<210> SEQ ID NO 10
<211> LENGTH: 401
<212> TYPE: PRT
<213> ORGANISM: Artificial Sequence
<220> FEATURE:
<223> OTHER INFORMATION: Synthesized

<400> SEQUENCE: 10

```
Phe Tyr Pro Gly Ser Gly Asn Ile Arg Tyr Asn Glu Lys Ile Lys Gly
1               5                   10                  15

Arg Val Thr Met Thr Arg Asp Thr Ser Thr Ser Thr Val Tyr Met Glu
            20                  25                  30

Leu Ser Ser Leu Arg Ser Glu Asp Thr Ala Val Tyr Tyr Cys Ala Arg
        35                  40                  45

His Gly Glu Leu Gly Gly Gly Tyr Phe Phe Asp Tyr Trp Gly Gln Gly
    50                  55                  60

Thr Thr Val Thr Val Ser Ser Ala Ser Thr Lys Gly Pro Ser Val Phe
65                  70                  75                  80

Pro Leu Ala Pro Ser Ser Lys Ser Thr Ser Gly Gly Thr Ala Ala Leu
                85                  90                  95

Gly Cys Leu Val Lys Asp Tyr Phe Pro Glu Pro Val Thr Val Ser Trp
            100                 105                 110

Asn Ser Gly Ala Leu Thr Ser Gly Val His Thr Phe Pro Ala Val Leu
        115                 120                 125

Gln Ser Ser Gly Leu Tyr Ser Leu Ser Ser Val Val Thr Val Pro Ser
    130                 135                 140

Ser Ser Leu Gly Thr Gln Thr Tyr Ile Cys Asn Val Asn His Lys Pro
145                 150                 155                 160

Ser Asn Thr Lys Val Asp Lys Lys Val Glu Pro Lys Ser Cys Asp Lys
                165                 170                 175

Thr His Thr Cys Pro Pro Cys Pro Ala Pro Glu Leu Leu Gly Gly Pro
            180                 185                 190
```

```
Ser Val Phe Leu Phe Pro Pro Lys Pro Lys Asp Thr Leu Met Ile Ser
            195                 200                 205
Arg Thr Pro Glu Val Thr Cys Val Val Val Asp Val Ser His Glu Asp
    210                 215                 220
Pro Glu Val Lys Phe Asn Trp Tyr Val Asp Gly Val Glu Val His Asn
225                 230                 235                 240
Ala Lys Thr Lys Pro Arg Glu Glu Gln Tyr Ala Ser Thr Tyr Arg Val
                245                 250                 255
Val Ser Val Leu Thr Val Leu His Gln Asp Trp Leu Asn Gly Lys Glu
            260                 265                 270
Tyr Lys Cys Lys Val Ser Asn Lys Ala Leu Pro Ala Pro Ile Glu Lys
        275                 280                 285
Thr Ile Ser Lys Ala Lys Gly Gln Pro Arg Glu Pro Gln Val Tyr Thr
    290                 295                 300
Leu Pro Pro Ser Arg Glu Glu Met Thr Lys Asn Gln Val Ser Leu Thr
305                 310                 315                 320
Cys Leu Val Lys Gly Phe Tyr Pro Ser Asp Ile Ala Val Glu Trp Glu
                325                 330                 335
Ser Asn Gly Gln Pro Glu Asn Asn Tyr Lys Thr Thr Pro Pro Val Leu
            340                 345                 350
Asp Ser Asp Gly Ser Phe Phe Leu Tyr Ser Lys Leu Thr Val Asp Lys
        355                 360                 365
Ser Arg Trp Gln Gln Gly Asn Val Phe Ser Cys Ser Val Met His Glu
    370                 375                 380
Ala Leu His Asn His Tyr Thr Gln Lys Ser Leu Ser Leu Ser Pro Gly
385                 390                 395                 400
Lys

<210> SEQ ID NO 11
<211> LENGTH: 15
<212> TYPE: DNA
<213> ORGANISM: Artificial Sequence
<220> FEATURE:
<223> OTHER INFORMATION: Synthesized

<400> SEQUENCE: 11
aagtacatca tccac                                                    15

<210> SEQ ID NO 12
<211> LENGTH: 51
<212> TYPE: DNA
<213> ORGANISM: Artificial Sequence
<220> FEATURE:
<223> OTHER INFORMATION: Synthesized

<400> SEQUENCE: 12
tggttctacc ctggttctgg caacatccgg tacaacgaga agatcaaggg c             51

<210> SEQ ID NO 13
<211> LENGTH: 36
<212> TYPE: DNA
<213> ORGANISM: Artificial Sequence
<220> FEATURE:
<223> OTHER INFORMATION: Synthesized

<400> SEQUENCE: 13
cacggagagc tgggcggagg ctacttcttc gactac                             36

<210> SEQ ID NO 14
```

```
<211> LENGTH: 90
<212> TYPE: DNA
<213> ORGANISM: Artificial Sequence
<220> FEATURE:
<223> OTHER INFORMATION: Synthesized

<400> SEQUENCE: 14
gaggtgcagc tggtgcagag cggcgccgag gtgaagaaac ctggcgcctc cgtgaaggtg    60
agctgcaagg cctccggcta caccttcacc                                     90

<210> SEQ ID NO 15
<211> LENGTH: 42
<212> TYPE: DNA
<213> ORGANISM: Artificial Sequence
<220> FEATURE:
<223> OTHER INFORMATION: Synthesized

<400> SEQUENCE: 15
tgggtgcggc aagcccctgg acagggactg gaatggatgg gc                       42

<210> SEQ ID NO 16
<211> LENGTH: 96
<212> TYPE: DNA
<213> ORGANISM: Artificial Sequence
<220> FEATURE:
<223> OTHER INFORMATION: Synthesized

<400> SEQUENCE: 16
agggtgacca tgacccggga caccagcacc tccaccgtgt acatggagct gtcctccctg    60
aggagcgagg acaccgccgt gtattactgc gctagg                              96

<210> SEQ ID NO 17
<211> LENGTH: 33
<212> TYPE: DNA
<213> ORGANISM: Artificial Sequence
<220> FEATURE:
<223> OTHER INFORMATION: Synthesized

<400> SEQUENCE: 17
tggggccagg gcacaaccgt gaccgtgtcc tcc                                 33

<210> SEQ ID NO 18
<211> LENGTH: 5
<212> TYPE: PRT
<213> ORGANISM: Artificial Sequence
<220> FEATURE:
<223> OTHER INFORMATION: Synthesized

<400> SEQUENCE: 18

Lys Tyr Ile Ile His
1               5

<210> SEQ ID NO 19
<211> LENGTH: 17
<212> TYPE: PRT
<213> ORGANISM: Artificial Sequence
<220> FEATURE:
<223> OTHER INFORMATION: Synthesized

<400> SEQUENCE: 19

Trp Phe Tyr Pro Gly Ser Gly Asn Ile Arg Tyr Asn Glu Lys Ile Lys
1               5                   10                  15

Gly
```

```
<210> SEQ ID NO 20
<211> LENGTH: 12
<212> TYPE: PRT
<213> ORGANISM: Artificial Sequence
<220> FEATURE:
<223> OTHER INFORMATION: Synthesized

<400> SEQUENCE: 20

His Gly Glu Leu Gly Gly Gly Tyr Phe Phe Asp Tyr
1               5                   10

<210> SEQ ID NO 21
<211> LENGTH: 30
<212> TYPE: PRT
<213> ORGANISM: Artificial Sequence
<220> FEATURE:
<223> OTHER INFORMATION: Synthesized

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 22
<211> LENGTH: 14
<212> TYPE: PRT
<213> ORGANISM: Artificial Sequence
<220> FEATURE:
<223> OTHER INFORMATION: Synthesized

<400> SEQUENCE: 22

Trp Val Arg Gln Ala Pro Gly Gln Gly Leu Glu Trp Met Gly
1               5                   10

<210> SEQ ID NO 23
<211> LENGTH: 32
<212> TYPE: PRT
<213> ORGANISM: Artificial Sequence
<220> FEATURE:
<223> OTHER INFORMATION: Synthesized

<400> SEQUENCE: 23

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: Synthesized

<400> SEQUENCE: 24

Trp Gly Gln Gly Thr Thr Val Thr Val Ser Ser
1               5                   10

<210> SEQ ID NO 25
<211> LENGTH: 642
<212> TYPE: DNA
<213> ORGANISM: Artificial Sequence
<220> FEATURE:
<223> OTHER INFORMATION: Synthesized

<400> SEQUENCE: 25
```

```
gatatccagc tgacccagag cccctccttt ctgtccgcct ccgtgggcga cagggtgacc        60
atcacctgca gggccagctc cagcgtgagc aacatcccac ggtatcaaca gaagcctggc       120
aaggccccca agccctggat ctacgccacc tccaacctgg ccagcggcgt gcctagcagg       180
ttcagcggtt ctggctccgg caccgagttc accctgacca tctcctccct gcagcccgag       240
gacttcgcca cctactactg ccagcagtgg tccagcaacc ccctgacctt tggccagggc       300
accaagctgg agatcaagag gactgtggct gcaccatctg tcttcatctt cccgccatct       360
gatgagcagt tgaaatctgg aactgcctct gttgtgtgcc tgctgaataa cttctatccc       420
agagaggcca agtacagtg gaaggtggat aacgccctcc aatcgggtaa ctcccaggag       480
agtgtcacag agcaggacag caaggacagc acctacagcc tcagcagcac cctgacgctg       540
agcaaagcag actacgagaa acacaaagtc tacgcctgcg aagtcaccca tcagggcctg       600
agctcgcccg tcacaaagag cttcaacagg ggagagtgtt aa                          642
```

<210> SEQ ID NO 26
<211> LENGTH: 213
<212> TYPE: PRT
<213> ORGANISM: Artificial Sequence
<220> FEATURE:
<223> OTHER INFORMATION: Synthesized

<400> SEQUENCE: 26

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Ser Asn Ile
            20                  25                  30

His Trp Tyr Gln Gln Lys Pro Gly Lys Ala Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 27
<211> LENGTH: 30
<212> TYPE: DNA

<213> ORGANISM: Artificial Sequence
<220> FEATURE:
<223> OTHER INFORMATION: Synthesized

<400> SEQUENCE: 27
agggccagct ccagcgtgag caacatccac    30

<210> SEQ ID NO 28
<211> LENGTH: 21
<212> TYPE: DNA
<213> ORGANISM: Artificial Sequence
<220> FEATURE:
<223> OTHER INFORMATION: Synthesized

<400> SEQUENCE: 28
gccacctcca acctggccag c    21

<210> SEQ ID NO 29
<211> LENGTH: 27
<212> TYPE: DNA
<213> ORGANISM: Artificial Sequence
<220> FEATURE:
<223> OTHER INFORMATION: Synthesized

<400> SEQUENCE: 29
cagcagtggt ccagcaaccc cctgacc    27

<210> SEQ ID NO 30
<211> LENGTH: 69
<212> TYPE: DNA
<213> ORGANISM: Artificial Sequence
<220> FEATURE:
<223> OTHER INFORMATION: Synthesized

<400> SEQUENCE: 30
gatatccagc tgacccagag cccctccttt ctgtccgcct ccgtgggcga cagggtgacc    60
atcacctgc    69

<210> SEQ ID NO 31
<211> LENGTH: 45
<212> TYPE: DNA
<213> ORGANISM: Artificial Sequence
<220> FEATURE:
<223> OTHER INFORMATION: Synthesized

<400> SEQUENCE: 31
tggtatcaac agaagcctgg caaggccccc aagccctgga tctac    45

<210> SEQ ID NO 32
<211> LENGTH: 96
<212> TYPE: DNA
<213> ORGANISM: Artificial Sequence
<220> FEATURE:
<223> OTHER INFORMATION: Synthesized

<400> SEQUENCE: 32
ggcgtgccta gcaggttcag cggttctggc tccggcaccg agttcaccct gaccatctcc    60
tccctgcagc ccgaggactt cgccacctac tactgc    96

<210> SEQ ID NO 33
<211> LENGTH: 33
<212> TYPE: DNA
<213> ORGANISM: Artificial Sequence
<220> FEATURE:
<223> OTHER INFORMATION: Synthesized

<400> SEQUENCE: 33
tttggccagg gcaccaagct ggagatcaag agg              33

<210> SEQ ID NO 34
<211> LENGTH: 10
<212> TYPE: PRT
<213> ORGANISM: Artificial Sequence
<220> FEATURE:
<223> OTHER INFORMATION: Synthesized

<400> SEQUENCE: 34

Arg Ala Ser Ser Ser Val Ser Asn Ile His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthesized

<400> SEQUENCE: 35

Ala Thr Ser Asn Leu Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized

<400> SEQUENCE: 36

Gln Gln Trp Ser Ser Asn Pro Leu Thr
1               5

<210> SEQ ID NO 37
<211> LENGTH: 23
<212> TYPE: PRT
<213> ORGANISM: Artificial Sequence
<220> FEATURE:
<223> OTHER INFORMATION: Synthesized

<400> SEQUENCE: 37

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 38
<211> LENGTH: 15
<212> TYPE: PRT
<213> ORGANISM: Artificial Sequence
<220> FEATURE:
<223> OTHER INFORMATION: Synthesized

<400> SEQUENCE: 38

Trp Tyr Gln Gln Lys Pro Gly Lys Ala Pro Lys Pro Trp Ile Tyr
1               5                   10                  15

<210> SEQ ID NO 39
<211> LENGTH: 32
<212> TYPE: PRT
<213> ORGANISM: Artificial Sequence
<220> FEATURE:

-continued

<223> OTHER INFORMATION: Synthesized

<400> SEQUENCE: 39

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: Synthesized

<400> SEQUENCE: 40

Phe Gly Gln Gly Thr Lys Leu Glu Ile Lys Arg
1               5                   10

<210> SEQ ID NO 41
<211> LENGTH: 642
<212> TYPE: DNA
<213> ORGANISM: Artificial Sequence
<220> FEATURE:
<223> OTHER INFORMATION: Synthesized

<400> SEQUENCE: 41

```
gatatccagc tgacccagag cccctccttt ctgtccgcct ccgtgggcga cagggtgacc      60
atcacctgca gggccagctc caagacgggg aacatccact ggtatcaaca gaagcctggc     120
aaggccccca agccctggat ctacgccacc tccaacctgg ccagcggcgt gcctagcagg     180
ttcagcggtt ctggctccgg caccgagttc accctgacca tctcctccct gcagcccgag     240
gacttcgcca cctactactg ccagcagtgg tccagcaacc cctgaccctt tggccagggc     300
accaagctgg agatcaagag gactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt aa                       642
```

<210> SEQ ID NO 42
<211> LENGTH: 213
<212> TYPE: PRT
<213> ORGANISM: Artificial Sequence
<220> FEATURE:
<223> OTHER INFORMATION: Synthesized

<400> SEQUENCE: 42

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Lys Thr Gly Asn Ile
            20                  25                  30

His Trp Tyr Gln Gln Lys Pro Gly Lys Ala Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 43
<211> LENGTH: 321
<212> TYPE: DNA
<213> ORGANISM: Artificial Sequence
<220> FEATURE:
<223> OTHER INFORMATION: Synthesized

<400> SEQUENCE: 43
gatatccagc tgacccagag ccctcctttt ctgtccgcct ccgtgggcga cagggtgacc    60
atcacctgca gggccagctc caagacgggg aacatccact ggtatcaaca gaagcctggc   120
aaggccccca agccctggat ctacgccacc tccaacctgg ccagcggcgt gcctagcagg   180
ttcagcggtt ctggctccgg caccgagttc accctgacca tctcctccct gcagcccgag   240
gacttcgcca cctactactg ccagcagtgg tccagcaacc ccctgacctt tggccagggc   300
accaagctgg agatcaagag g                                              321

<210> SEQ ID NO 44
<211> LENGTH: 30
<212> TYPE: DNA
<213> ORGANISM: Artificial Sequence
<220> FEATURE:
<223> OTHER INFORMATION: Synthesized

<400> SEQUENCE: 44
agggccagct ccaagacggg gaacatccac                                     30

<210> SEQ ID NO 45
<211> LENGTH: 107
<212> TYPE: PRT
<213> ORGANISM: Artificial Sequence
<220> FEATURE:
<223> OTHER INFORMATION: Synthesized

<400> SEQUENCE: 45

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Lys Thr Gly Asn Ile
            20                  25                  30

His Trp Tyr Gln Gln Lys Pro Gly Lys Ala Pro Lys Pro Trp Ile Tyr

```
                  35                  40                  45

Ala Thr Ser Asn Leu Ala Ser Gly Val Pro Ser Arg Phe Ser Gly Ser
         50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                 85                  90                  95

Phe Gly Gln Gly Thr Lys Leu Glu Ile Lys Arg
            100                 105
```

<210> SEQ ID NO 46
<211> LENGTH: 10
<212> TYPE: PRT
<213> ORGANISM: Artificial Sequence
<220> FEATURE:
<223> OTHER INFORMATION: Synthesized

<400> SEQUENCE: 46

```
Arg Ala Ser Ser Lys Thr Gly Asn Ile His
1               5                   10
```

<210> SEQ ID NO 47
<211> LENGTH: 642
<212> TYPE: DNA
<213> ORGANISM: Artificial Sequence
<220> FEATURE:
<223> OTHER INFORMATION: Synthesized

<400> SEQUENCE: 47

```
gatatccagc tgacccagag cccctccttt ctgtccgcct ccgtgggcga cagggtgacc      60
atcacctgca gggccagctc cggcgcgtcc aacatccact ggtatcaaca gaagcctggc     120
aaggccccca agccctggat ctacgccacc tccaacctgg ccagcggcgt gcctagcagg     180
ttcagcggtt ctggctccgg caccgagttc accctgacca tctcctccct gcagcccgag     240
gacttcgcca cctactactg ccagcagtgg tccagcaacc cctgaccttt ggccagggc      300
accaagctgg agatcaagag gactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag      480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt aa                        642
```

<210> SEQ ID NO 48
<211> LENGTH: 213
<212> TYPE: PRT
<213> ORGANISM: Artificial Sequence
<220> FEATURE:
<223> OTHER INFORMATION: Synthesized

<400> SEQUENCE: 48

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Gly Ala Ser Asn Ile
             20                  25                  30

His Trp Tyr Gln Gln Lys Pro Gly Lys Ala Pro Lys Pro Trp Ile Tyr
         35                  40                  45

Ala Thr Ser Asn Leu Ala Ser Gly Val Pro Ser Arg Phe Ser Gly Ser
```

```
            50                  55                  60
Gly Ser Gly Thr Glu Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 49
<211> LENGTH: 321
<212> TYPE: DNA
<213> ORGANISM: Artificial Sequence
<220> FEATURE:
<223> OTHER INFORMATION: Synthesized

<400> SEQUENCE: 49
gatatccagc tgacccagag ccctcctttt ctgtccgcct ccgtgggcga cagggtgacc      60
atcacctgca gggccagctc cggcgcgtcc aacatccact ggtatcaaca gaagcctggc     120
aaggccccca agccctggat ctacgccacc tccaacctgg ccagcggcgt gcctagcagg     180
ttcagcggtt ctggctccgg caccgagttc accctgacca tctcctccct gcagcccgag     240
gacttcgcca cctactactg ccagcagtgg tccagcaacc cctgaccttt tggccagggc     300
accaagctgg agatcaagag g                                               321

<210> SEQ ID NO 50
<211> LENGTH: 30
<212> TYPE: DNA
<213> ORGANISM: Artificial Sequence
<220> FEATURE:
<223> OTHER INFORMATION: Synthesized

<400> SEQUENCE: 50
agggccagct ccggcgcgtc caacatccac                                       30

<210> SEQ ID NO 51
<211> LENGTH: 107
<212> TYPE: PRT
<213> ORGANISM: Artificial Sequence
<220> FEATURE:
<223> OTHER INFORMATION: Synthesized

<400> SEQUENCE: 51

Asp Ile Gln Leu Thr Gln Ser Pro Ser Phe Leu Ser Ala Ser Val Gly
  1               5                  10                  15
```

```
Asp Arg Val Thr Ile Thr Cys Arg Ala Ser Ser Gly Ala Ser Asn Ile
             20                  25                  30

His Trp Tyr Gln Gln Lys Pro Gly Lys Ala Pro Lys Pro Trp Ile Tyr
         35                  40                  45

Ala Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                 85                  90                  95

Phe Gly Gln Gly Thr Lys Leu Glu Ile Lys Arg
            100                 105
```

```
<210> SEQ ID NO 52
<211> LENGTH: 10
<212> TYPE: PRT
<213> ORGANISM: Artificial Sequence
<220> FEATURE:
<223> OTHER INFORMATION: Synthesized

<400> SEQUENCE: 52

Arg Ala Ser Ser Gly Ala Ser Asn Ile His
 1               5                  10
```

```
<210> SEQ ID NO 53
<211> LENGTH: 97
<212> TYPE: DNA
<213> ORGANISM: Artificial Sequence
<220> FEATURE:
<223> OTHER INFORMATION: Synthesized

<400> SEQUENCE: 53
ggggtaccgc cgccaccatg gagacagaca cactcctgct atgggtactg ctgctctggg      60
ttccaggttc cactggtgag gtgcagctgg tgcagag                              97
```

```
<210> SEQ ID NO 54
<211> LENGTH: 34
<212> TYPE: DNA
<213> ORGANISM: Artificial Sequence
<220> FEATURE:
<223> OTHER INFORMATION: Synthesized

<400> SEQUENCE: 54
ggctctagat tatcactttc caggggacag tgac                                 34
```

```
<210> SEQ ID NO 55
<211> LENGTH: 97
<212> TYPE: DNA
<213> ORGANISM: Artificial Sequence
<220> FEATURE:
<223> OTHER INFORMATION: Synthesized

<400> SEQUENCE: 55
ggggtaccgc cgccaccatg gagacagaca cactcctgct atgggtactg ctgctctggg      60
ttccaggttc cactggtgat atccagctga cccagag                              97
```

```
<210> SEQ ID NO 56
<211> LENGTH: 32
<212> TYPE: DNA
<213> ORGANISM: Artificial Sequence
<220> FEATURE:
<223> OTHER INFORMATION: Synthesized
```

```
<400> SEQUENCE: 56
ggctctagat taacactctc ccctgttgaa gc                                    32
```

ANTI-HUMAN PD-L1 HUMANIZED MONOCLONAL ANTIBODY AND APPLICATION THEREOF

This application claims priority for the Chinese patent application "Anti-Human PD-L1 Humanized Monoclonal Antibody and Its Applications", with filing date Friday, May 20, 2016 and application number 201610340678.3. All the contents of present invention are combined in this application by reference.

REFERENCE TO SEQUENCE LISTING SUBMITTED ELECTRONICALLY

The official copy of the sequence listing is submitted electronically via EFS-Web as an ASCII formatted sequence listing with a file named "KGI1-PAU05NS--Seq_List.txt", created on Sep. 11, 2018, and having a size of 32 kilobytes and is filed concurrently with the specification. The sequence listing contained in this ASCII formatted document is part of the specification and is herein incorporated by reference in its entirety.

FIELD OF THE INVENTION

The present invention relates to the biomedicine field, in particular to an anti-human PD-L1 humanized monoclonal antibody and its applications.

BACKGROUND OF THE INVENTION

The adaptive response of human immune system mainly includes the activation, differentiation and proliferation of T-cells and B-cells. Among them, the activation of T-cell function is regulated by two types of signals. One is the antigen-specific signal provided by T-cell receptor (TCR) recognizing the MHC-antigen complex on antigen-presenting cells (APC). The other is the co-stimulation and inhibition signal formed between T-cells and immuno-checkpoint proteins expressed on APC cells. This kind of co-stimulatory or inhibitory signal often plays an important role in the proliferation, differentiation and activation of T-cells. Normally, the immuno-checkpoint is critical in maintaining body's self-tolerance (preventing autoimmunity) and protecting the body from being infected by external pathogens.

PD-L1/PD1 signal pathway is a very important co-inhibitory signal pathway in immune response. Programmed death receptor-1 (PD-1, also known as CD279) has two glycoprotein ligands on cell surface: PD-L1 (also known as B7-H1, CD274) and PD-L2 (also known as B7-DC, CD273).

The human PD-L1 gene encodes 290 amino acids (including 1-18 amino acids as signal peptides, 19-238 amino acids as extracellular segments, 239-259 amino acids as transmembrane segments, and 260-290 amino acids as intracellular segments). It is a type I membrane protein that is generally expressed in T-cells, B-cells, dendritic cells, macrophages and many non-hematopoietic cells. Studies have shown that when PD-L1 binds to PD-1, protein tyrosine phosphatases SHP-1 and SHP-2 with SH2 domain will be supplemented. These two phosphatases can reduce the phosphorylation of the immunoreceptor tyrosine activating motif (ITAM) of the CD3_chain, weaken the activation of ZAP-70, and inhibit the downstream signal transduction of TCR, thus co-inhibiting the activation of T cells. This negative regulatory effect can prevent the over-activation of effector T-cells leading to autoimmune damage.

However, if PD-L1 is expressed in tumor tissues, the killing effect of the immune system on tumor tissues can be weakened by binding to PD-1 of immune cells. PD-L1 has been found to be highly expressed in many tumor tissues (gastric cancer, breast cancer, pancreatic cancer, ovarian cancer, lung cancer, prostate cancer, malignant melanoma, etc.) and in bone marrow cells in tumor-infiltrating microenvironment. The expression of PD-L1 is also closely related to the poor prognosis of melanoma, breast cancer and ovarian cancer. If the link reaction between PD-L1 and PD-1 is blocked, the effector function of T-cells can be restored. Tumors, such as melanoma, can express PD-L1 at the beginning of their formation, thus possessing innate immune escape ability. The expression level of PD-L1 is often closely related to the prognosis of the disease.

Therefore, the expression of PD-L1 has become a vital biomarker in the use of immunotherapy targeting the PD-1/PD-L1 signal pathway, helping researchers to speculate which patients are more likely to respond to such immunotherapy.

At present, the antibody drugs targeted at PD-L1 have shown excellent application prospects clinically. For example, Roche's all-human IgG1 monoclonal antibody MPDL3280A can block the binding of PD-L1 to PD-1 and CD80, and weaken the antibody-mediated cytotoxicity by engineering transformation on its Fc fragments. In Phase I clinical trials, patients with metastatic bladder cancer with positive PD-L1 expression develop a response rate of 52% after 12 weeks of MPDL 3280A treatment. Adverse reactions just include low-grade fatigue and nausea, and there is no evidence of nephrotoxicity. Continuous response to drugs is also observed in melanoma patients, so MPDL3280A is granted with the breakthrough treatment status by FDA. Its clinical research is also being carried out in patients with advanced renal cell carcinoma and non-small cell lung cancer. Another PD-L1 monoclonal antibody, Avelumab, co-developed by Pfizer and Merck, is also being evaluated for efficacy and safety in patients with metastatic Merkel cell carcinoma.

Not only that, studies have shown that some viral infections are also closely related to PD-L1/PD-1 signal pathway. For example, in chronic HIV infection, PD-1 is found to be highly expressed on the surface of HIV-specific CD8+T cells. The virus inhibits the activity of HIV-specific CD8+T cells by activating the PD-L1/PD-1 signal pathway. The secretion of cytokines and the proliferation of T cells are greatly weakened, resulting in acquired immunodeficiency. Therefore, blocking the PD-L1/PD-1 signal pathway, in the treatment of such diseases, also has considerable application value.

Consequently, the development of drugs with the ability to block the PD-L1/PD-1 signal pathway will bring new methods for the treatment of tumor, viral infection and a variety of immune system-related diseases, with great application potential and market value.

SUMMARY OF THE INVENTION

To solve these technical problems, the present invention aims to provide an anti-human PD-L1 humanized monoclonal antibody with good specificity, high affinity and stability.

The first aspect of the invention relates to an anti-human PD-L1 humanized monoclonal antibody or an antigen binding part thereof, which comprises a CDR region selected from a group of the following:
(1) The sequences of heavy chains CDR1, CDR2 and CDR3 are shown as SEQ ID NO: 18-20, respectively.

The sequences of light chains CDR1, CDR2 and CDR3 are shown as SEQ ID NO: 34-36, respectively, or includes sequences that bind antigenic epitopes same to above sequences;

(2) The sequences of heavy chains CDR1, CDR2 and CDR3 are shown as SEQ ID NO: 18-20, respectively. The sequences of light chains CDR1, CDR2 and CDR3 are shown as SEQ ID NO: 45, 35 and 36, respectively, or includes sequences that bind antigenic epitopes same to above sequences;

(3) The sequences of heavy chains CDR1, CDR2 and CDR3 are shown as SEQ ID NO: 18-20, respectively. The sequences of light chains CDR1, CDR2 and CDR3 are shown as SEQ ID NO: 52, 35 and 36, respectively, or includes sequences that bind antigenic epitopes same to above sequences.

Further, the anti-human PD-L1 humanized monoclonal antibody or its antigen binding part in the invention, also includes sequences selected from the following framework regions of heavy chain variable region: FR1, FR2, FR3 and FR4, as shown in SEQ ID NO: 21-24, respectively, or other sequences that having greater than 70%, 80%, 85%, 90%, 95%, 99% identity to them, respectively.

Further, the anti-human PD-L1 humanized monoclonal antibody or its antigen binding part in the invention, also includes sequences selected from the following framework regions of light chain variable region: FR1, FR2, FR3 and FR4, as shown in SEQ ID NO: 37-40, respectively, or other sequences that having greater than 70%, 80%, 85%, 90%, 95%, 99% identity to them, respectively.

Further, the anti-human PD-L1 humanized monoclonal antibody or its antigen binding part in the invention, includes sequences selected from the following heavy chain variable region, as shown in SEQ ID NO: 6, or includes sequences that bind antigenic epitopes same to above sequences.

Further, the anti-human PD-L1 humanized monoclonal antibody or its antigen binding part in the invention, also includes sequences selected from the following light chain variable regions, as shown in SEQ ID NO: 8, 45 or 51, or other sequences that having greater than 70%, 80%, 85%, 90%, 95%, 99% identity to above sequences, respectively.

Specifically, for the anti-human PD-L1 humanized monoclonal antibody or its antigen binding part in the invention, the sequence of heavy chain is as shown in SEQ ID NO: 10.

Specifically, for the anti-human PD-L1 humanized monoclonal antibody or its antigen binding part in the invention, the sequence of light chain is as shown in SEQ ID NO: 26, 42 or 48.

A nucleic acid molecule according to the second aspect of the invention contains a nucleic acid sequence that is capable of encoding an antibody heavy chain variable region, which comprises an amino acid sequence selected from the following group:

(1) SEQ ID NO: 18-20;
(2) Sequence that satisfies at least one of the following two requirements when compared with the sequence a) binding to the same antigenic epitope; b) identity greater than 70%, 80%, 85%, 90% or 97%.

Further, the heavy chain variable region contains an amino acid sequence selected from the following group:
SEQ ID NO: 6, or the sequence that satisfies at least one of the following three requirements when compared with the sequence (1): a) binding to the same antigenic epitope; b) identity greater than 70%, 80%, 85%, 90% or 97%; c) containing substitution for one or more nucleotides in the framework region of the above-mentioned sequence.

In the embodiments of the invention, the nucleic acid molecules contain selected sequences as shown in SEQ ID NO: 5.

Further, the nucleic acid molecule contains selected sequences as shown in SEQ ID NO: 9.

A nucleic acid molecule according to the third aspect of the invention contains a nucleic acid sequence that is capable of encoding an antibody light chain variable region, which comprises an amino acid sequence selected from the following group:

(1) SEQ ID NO: 34-36;
(2) SEQ ID NO: 46, 35 or 36;
(3) SEQ ID NO: 52, 35 or 36;
(4) Sequence that satisfies at least one of the following two requirements when compared with the sequences (1)-(3): a) binding to the same antigenic epitope; b) identity greater than 70%, 80%, 85%, 90% or 97%.

Further, the light chain variable region contains an amino acid sequence selected from the following group:
SEQ ID NO: 8, 45 or 51, or the sequence that satisfies at least one of the following three requirements when compared with abovementioned sequences: a) binding to the same antigenic epitope; b) identity greater than 70%, 80%, 85%, 90% or 97%; c) containing substitution for one or more nucleotides in the framework region of the above-mentioned sequence.

In the embodiments of the invention, the nucleic acid molecules contain selected sequences as shown in SEQ ID NO: 7, 43 or 49.

Further, the nucleic acid molecule contains selected sequences as shown in SEQ ID NO: 25, 41 or 47.

The fourth aspect of the invention relates to a carrier which contains nucleic acid molecules as described in the second or third aspect of the invention.

Further, the carrier referred to in the invention contains any nucleic acid molecule as described in the second and third aspects of the invention.

The fifth aspect of the invention relates to host cells, which contain any nucleic acid molecule as described in the second or third aspect of the invention, or any carrier as described in the fourth aspect of the invention.

The sixth aspect of the invention relates to conjugates, which contain any anti-human PD-L1 humanized monoclonal antibody or its antigen binding part as described in the first aspect of the invention, and other bioactive substances. The anti-human PD-L1 humanized monoclonal antibody or its antigen binding part is directly or through junction fragments, coupled with other bioactive substances.

In the embodiment of the invention, the other bioactive substances are selected from chemicals, toxins, peptides, enzymes, isotopes, or cytokines that can directly or indirectly inhibit cell growth or kill cells, or inhibit or kill cells by activating the immune response of organism for the treatment of tumors, or selected from other single or mixed substances with biological activity.

The seventh aspect of the invention relates to compositions (e.g. pharmaceutical composition), which contain any anti-human PD-L1 humanized monoclonal antibody or its antigen binding part as described in the first aspect of the invention, any nucleic acid molecule as described in the second or third aspect, any carrier as described in the fourth aspect, any host cell as described in the fifth aspect, or any conjugate as described in the sixth aspect, as well as optional pharmaceutically acceptable carriers or excipients, and optional other bioactive substances.

In accordance with any composition (e.g. pharmaceutical composition) as described in the seventh aspect of the invention, the other bioactive substances include, but are not limited to, other antibodies, fusion proteins or drugs (e.g. anti-tumor drugs, such as radiotherapy and chemotherapy drugs).

The invention also relates to diagnostic reagents or kits, which contain any anti-human PD-L1 humanized monoclonal antibody or its antigen-binding part as described in the first aspect of the invention. The diagnostic reagents or kits are used in vitro (e.g. cells or tissues) or in vivo (e.g. human or animal models) to diagnose diseases associated with PD-L1 (e.g. tumors or virus infection, such as virus infection or tumor with overexpression of PD-L1).

In the embodiment of the present invention, the tumors include, but are not limited to, lung cancer, ovarian cancer, colon cancer, rectal cancer, melanoma, renal cancer, bladder cancer, breast cancer, liver cancer, lymphoma, malignant hematopathy, head & neck cancer, glioma, gastric cancer, nasopharyngeal cancer, laryngeal cancer, cervical cancer, uterine body cancer, osteosarcoma, thyroid cancer, and prostatic cancer. The virus infections include, but are not limited to, acute, subacute or chronic HBV, HCV and HIV infections.

The invention also relates to any anti-human PD-L1 humanized monoclonal antibody or its antigen binding part as described in the first aspect of the invention, any nucleic acid molecule as described in the second or third aspect, any carrier as described in the fourth aspect, any host cell as described in the fifth aspect, any conjugate as described in the sixth aspect, or any composition as described in the seventh aspect which is used to prepare medicines for the prevention or treatment of PD-L1 associated diseases (e.g. tumors, microbial or virus infection, such as tumor or virus infection overexpression of PD-L1).

In the embodiment of the present invention, the tumors include, but are not limited to, lung cancer, ovarian cancer, colon cancer, rectal cancer, melanoma, renal cancer, bladder cancer, breast cancer, liver cancer, lymphoma, malignant hematopathy, head & neck cancer, glioma, gastric cancer, nasopharyngeal cancer, laryngeal cancer, cervical cancer, uterine body cancer, osteosarcoma, thyroid cancer, and prostatic cancer. The microbial infections include, but are not limited to, bacterial, fungal and protozoal infections. The virus infections include, but are not limited to, acute, subacute or chronic HBV, HCV and HIV infections.

The following is a further description of the invention, where unless otherwise specified, the scientific and technical terms used herein have meanings commonly understood by those skilled in the art. In addition, the terms used in this document, including those related to protein and nucleic acid chemistry, molecular biology, cell and tissue culture, microbiology, immunology and laboratory procedures, refer to terms or procedures widely used in their fields. The following terms are defined and explained here to ensure a better understanding of the present invention.

In the present invention, the term "antibody" refers to an immunoglobulin molecule normally consisted of two pairs of identical polypeptide chains, each with a "light" (L) chain and a "heavy" (H) chain. The light chains of antibody can be classified as κ and λ light chains. The heavy chains can be classified as µ, δ, γ, α and ε, with antibody isotypes defined as IgM, IgD, IgG, IgA and IgE, respectively. In light and heavy chains, the variable region and the constant region are linked with each other through the "J" region of about 12 or more amino acids, and the heavy chain also contains the "D" region of about three or more amino acids. Each heavy chain is consisted of a heavy chain variable region ($V_H$) and a heavy chain constant region ($C_H$). The heavy chain constant region is consisted of 3 domains ($C_H1$, $C_H2$ and $C_H3$). Each light chain is consisted of a light chain variable region ($V_L$) and a light chain constant region ($C_L$). The light chain constant region is consisted of a domain $C_L$. The constant region of antibody can mediate the binding of immunoglobulins to host tissues or factors, including various cells of the immune system (e.g. effector cells) and the first component of classical complement system (C1q). The $V_H$ and $V_L$ regions can also be subdivided into highly variable regions (called as complementary determinant regions (CDR)), amongst of which conservative regions known as framework regions (FR) are distributed. Each $V_H$ or $V_L$ region is consisted of three CDRs and four FRs arranged from the amino terminal to the carboxyl terminal in the following order: FR1, CDR1, FR2, CDR2, FR3, CDR3, FR4. The variable regions (V H and V L) of each heavy/light chain pair form antibody binding sites separately. The distribution of amino acids to regions or domains follows the definitions in Kabat Sequences of Proteins of Immunological Interest (National Institutes of Health, Bethesda, Md. (1987 and 1991)), or in Chothia&Lesk (1987) J. Mol. Biol. 196:901-917; Chothia et al. (1989) Nature 342: 878-883. The term "antibody" is not limited by any specific antibody production method. For example, it particularly includes recombinant antibodies, monoclonal antibodies and polyclonal antibodies. Antibodies can be of different types, such as IgG (e.g. IgG1, IgG2, IgG3 or IgG4 subtypes), IgA1, IgA2, IgD, IgE, or IgM antibody.

In the present invention, the term "antigen-binding part" of an antibody refers to one or more parts of a full-length antibody that retain the ability of binding the same antigen (e.g. PD-L1) of the antibody, so as to compete with the intact antibody for antigen specific binding. Usually, see Fundamental Immunology, Ch.7 (Paul, W., ed., 2nd Edition, Raven Press, N.Y. (1989)), which is incorporated in this article by citation for all purposes. The antigen binding part can be produced by recombinant DNA technology or by enzymatic or chemical cleavage of intact antibody. In some cases, the antigen binding part includes Fab, Fab', F (ab') 2, Fd, Fv, dAb, and complementary determinant region (CDR) fragments, single chain antibodies (e.g. scFv), chimeric antibodies, diabodies and such kind of peptides, which contain at least a part of the antibody sufficient to give the peptides a capacity for antigen specific binding.

With the above scheme, the present invention has at least the following advantages: the invention obtains an anti-human PD-L1 humanized monoclonal antibody with good specificity, high affinity and stability by screening, and the antibody can specifically bind to human PD-L1 instead of binding to other members of B728 family, and it can bind to active T-cells to strengthen the activation of T-cells, so it can significantly inhibit the growth of tumor.

The above description is only an overview of the technical scheme of the present invention. In order to have a better understanding of the technical means of the invention and to implement in accordance with the specifications, see following details based on good embodiments of the invention and the description of the figures.

EMBODIMENTS

Figure 1:
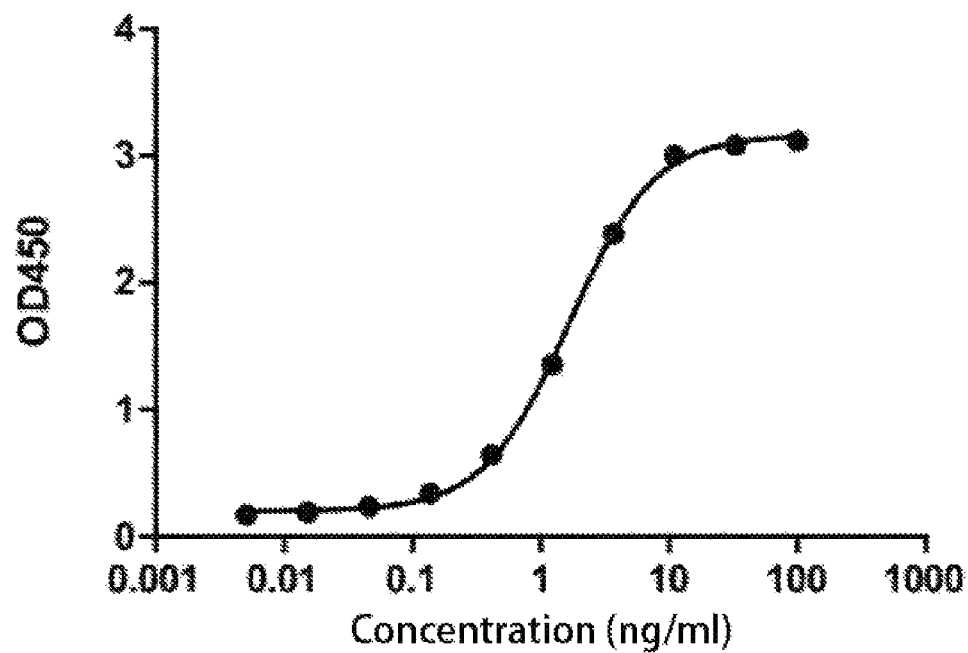
FIG. 1 shows the result of ELISA binding activity of mouse PD-L1 antibody.

The invention is described in detail as follows through Figures and embodiments. The following embodiments are used to illustrate the present invention, but not to limit the scope of the invention.

Embodiment 1: Screening of Mouse Antibody 1.1 Animal Immunity

The classical immunization schedule is used to immunize BALB/c mice. The immunogen is hPD-L1 (human PD-L1) protein (purchased from Beijing YiqiaoShenzhou Biotechnology Co., Ltd.) so that the mice can produce anti-hPD-L1 antibodies. The specific scheme is shown in Table 1:

TABLE 1

Animal Immunization Scheme for hPD-L1 Protein

| Step | Days | Method |
|---|---|---|
| Preimmune serum collection | −4 | Collect blood at orbital cavity, expect to obtainserum of 15-30 μL and store at −20° C. |
| Primary immunization | 0 | Amount of immunogen: 50 μg; injection method: IP (intraperitoneal injection); adjuvant: FCA (freund's complete adjuvant) |
| First boosted immunization | 14 | Amount of immunogen: 50 μg; injection method: IP (intraperitoneal injection); adjuvant: FIA (freund'sincomplete adjuvant) |
| Second boosted immunization | 35 | Amount of immunogen: 50 μg; injection method: IP (intraperitoneal injection); adjuvant: FIA (freund'sincomplete adjuvant) |
| Valence measurement by serum collection | 42 | Collect blood at orbital cavity, expect to obtainserum of 15-30 μL. Measure the serum titer of mouse by indirect ELISA assay. |
| Final immunization | 56 | Amount of immunogen: 50 μg; injection method: IV (intravenous injection) |
| Feeding cells preparation | 58 | Six mice needed for each time (aged about 10 weeks) 1. Remove eyeballs from unimmunized mice to collect blood. Separate the serum to use it as the negative control serum in antibody detection. Kill the mice by cervical dislocation, soak them in 75% ethyl alcohol for 5 min, and then fix them on dissecting table. 2. Use sterilizing tweezer to raise abdominal skin from posterior abdomen, so as to expose the peritoneum. Disinfect the peritoneum with alcohol wipes. 3. Inject 10 mL medium by syringe into the abdominal cavity, without passing through the intestinal canal. Fix the syringe with right hand to keep the needle staying in the abdominal cavity. Hold the alcohol wipe with left hand to flip the abdomen for 1 min, and then suck out the injected culture fluid so as to obtain cells effused from the abdominal cavity and use as the feeder cells. |
| Spleen harvest | 59 | Kill the mice to collect spleens. Put the spleens into a 10 mL plate with no serummedium. Use a needle to break the spleens and use a plunger to slightly press them, so as to collect immune spleen cells. Filter with a 200-mesh screen, centrifuge at 1200 rpm for 5 min, and remove supernatant. Use RBC lysate buffer to re-suspend the spleen cells, centrifuge at 1200 rpm for 5 min, then wash with serum-free medium for one time, and re-suspend by 20 mL serum-free medium. Count the cells and store them under 4° C. |

1.2 Cell Fusion and Screening of Hybridoma Cell

Before fusion, the state of mouse myeloma SP2/0 is adjusted to ensure that its growth density does not exceed $1.0 \times 10^6$ cells. The final immunization is carried out 3 days ahead of schedule, for which tail vein injection is used. The feeding cells are prepared 1 day ahead of schedule, with plate layout of $2.0 \times 10^4$ cells/well. By PEG fusion, the ratio of spleen cells to SP2/0 cells is between 10:1 and 5:1, and the number of spleen cells per well is up to $1.0 \times 10^5$. After 7 days of fusion, harvest the supernatant and replace the medium.

The harvested supernatant is first screened by direct ELISA binding method. After expansion on obtained positive clones, re-screen the supernatant.

Two rounds of re-screening are carried out through cell binding and inhibition experiments. The positive clones obtained by screening are subcloned by limited dilution method and arranged on 96-well plates, which are 5 clones/well, 2 clones/well and 1 clone/well. After 7 days of culture, the positive subclones are selected by direct ELISA binding experiment, and then expanded and preserved.

The specific steps involved in each experiment method are as follows:

A. ELISA Binding Method

Envelop hPD-L1-Fc on the plate, add gradient diluted antibody, incubate and wash it, and then add goat anti-mouse-HRP, perform coloration, and draw up the reaction curve by fitting of readings to calculate the EC50 value.

B. Cell Binding Experiment

Lay the over-expressed hPD-L1-Fc cells on the cell plate for culture inspection one day ahead of schedule. After closure on the next day, add gradient-diluted antibody, then anti-mouse-EU, and obtain the readings.

C. Cell Inhibition Experiment

Lay the over-expressed hPD-L1-Fc cells on the cell plate for culture inspection one day ahead of schedule. After closure on the next day, add gradient-diluted antibody, then PD1-Fc-Biotin, then Europium-labeled streptavidin, and obtain the readings.

1.3 Preparation and Activity Identification of Mouse Antibody

Inoculate the hybridoma cells of selected positive subclones into SFM medium for about 7 days. Collect the supernatant and purify it with Protein G purification column after centrifugal filtration. Then test the purified antibodies for ELISA binding activity, ELISA inhibitory activity, cell binding activity, and cell inhibitory activity. After screening, obtain a mouse anti-PD-L1 monoclonal antibody with the highest activity, and name it as mouse anti-PD-L1.

The specific steps involved in each experiment method are as follows:

A. ELISA Binding Activity

Envelop hPD-L1-Fc on the plate, add gradient diluted antibody, incubate and wash it, and then add goat anti-mouse-HRP, perform coloration, and draw up the reaction curve by fitting of readings (the results as shown in FIG. 1) to calculate the EC50 value. The binding activity EC50 to hPD-1 is 1.67 ng/mL.

B. ELISA Inhibitory Activity

Figure 2:
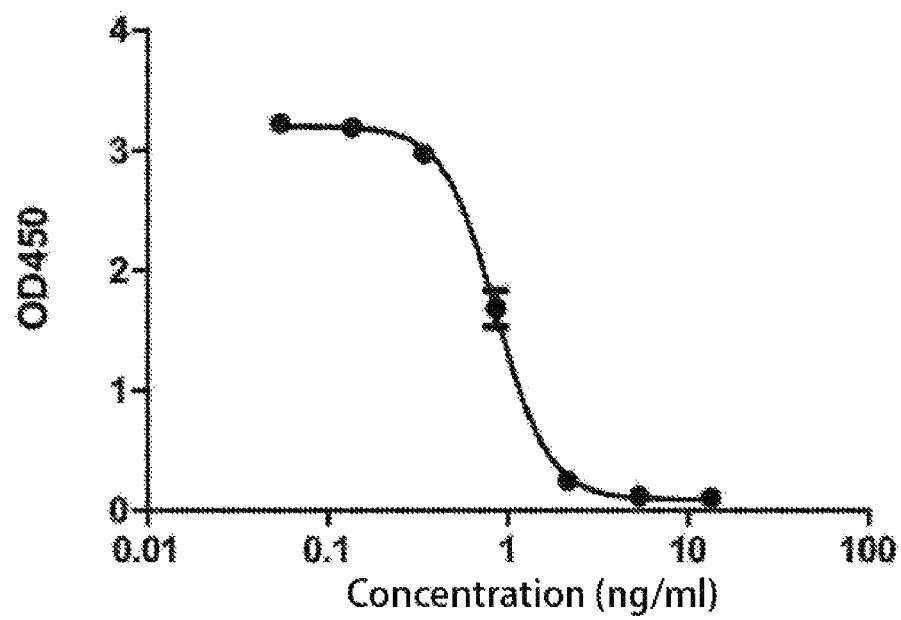
FIG. 2 shows the result of ELISA inhibitory activity of mouse PD-L1 antibody.

Incubate the gradient diluted antibody and a certain concentration of hPD-L1-Fc-Biotin, then add the mixture to the plate enveloped with hPD-L1-Fc. Add SA-HRP to the plate after incubating and washing. Then perform coloration. Draw up the reaction curve by fitting of readings (see FIG. 2 for results) to calculate the IC50 value. The inhibitory activity IC50 is 0.86 nM.

C. Cell Binding Activity

Figure 3:
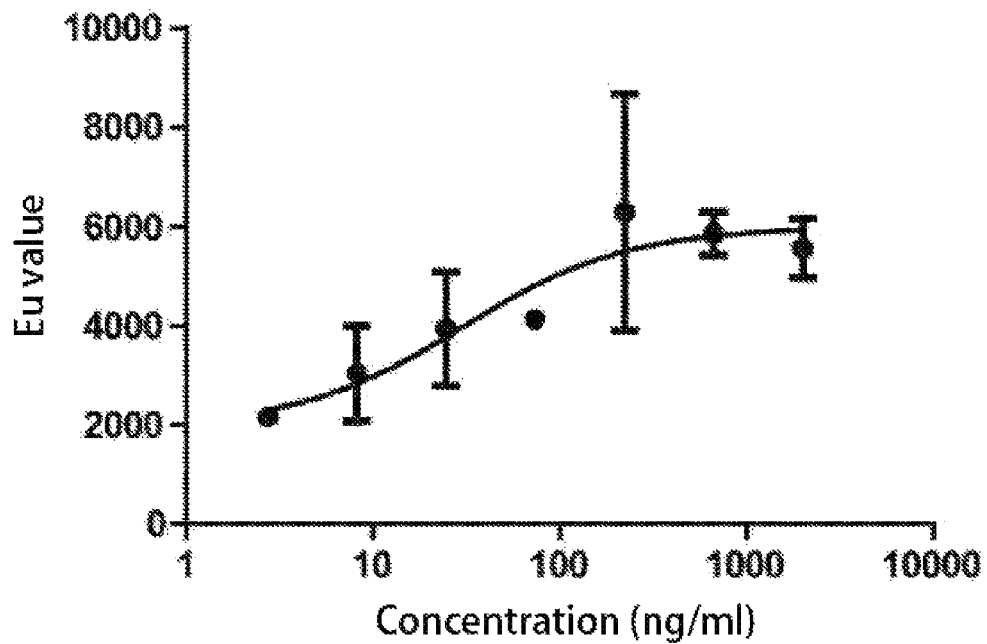
FIG. 3 shows the result of cell binding activity of mouse PD-L1 antibody.

Lay hPD-L1-Fc over-expressed cells on the cell plate for culture inspection one day ahead of schedule. After closure on the next day, add gradient-diluted antibody, then anti-mouse-EU. And then obtain the readings. Draw up the reaction curve by fitting of readings (see FIG. 3 for results) to calculate the cell binding activity EC50 which is 30.29 ng/mL.

D. Cell Inhibitory Activity

Figure 4:
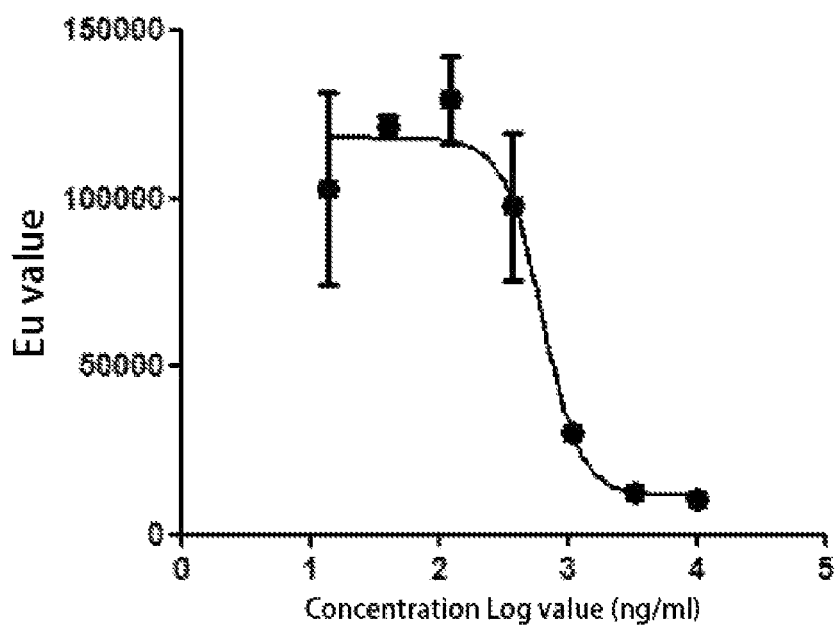
FIG. 4 shows the result of cell inhibitory activity of mouse PD-L1 antibody.

Lay PD1-27 (PD1 over-expressed CHO-K1 stable transfected cells) on the cell plate for culture inspection one day ahead of schedule. After closure on the next day, add gradient-diluted antibody, then PD1-Fc-Biotin, then Europium-labeled streptavidin, and obtain the readings. Draw up the reaction curve by fitting of readings (see FIG. 4 for results) to calculate the cell inhibitory activity IC50 which is 637.8 ng/mL.

Embodiment 2: Humanization and Affinity Maturation of Mouse Antibody 2.1 Acquisition of Mouse Antibody Genes Use Purelink RNA Micro kit to extract mouse anti-PD-L1 hybridoma total RNA, then use PrimeScript™ II 1st Strand cDNA Synthesis Kit to make the reverse transcription of total RNA and prepare cDNA. Use Leader primer to expand the variable regions of heavy and light chains separately. The reaction system and PCR conditions are shown in Tables 2 and 3, respectively.

TABLE 2

| PCR reaction system of mouse antibody gene cDNA | |
|---|---|
| Reagent name | Volume added |
| 10×Buffer | 5 µL |
| 10 µM dNTP Mix | 1 µL |
| 50 mM MgSO4 | 2 µL |
| Upstream and downstream primers | 1 µL for each |
| cDNA template | 1 µL |
| Taq | 0.2 µL |
| ddH2O | up to 50 µL |

TABLE 3

| PCR reaction conditions of mouse antibody gene cDNA | | |
|---|---|---|
| Temperature | Time | |
| 94° C. | 5 min | |
| 94° C. | 30 s | |
| 50° C. | 30 s | Totally 30 cycles |
| 68° C. | 45 s | |
| 68° C. | 7 min | |

Cool to 4° C.

The PCR results are analyzed by electrophoresis.

Add 0.5 µl LA Taq enzyme into the reaction tube containing expansion products and react 10 min at 72° C. After that, perform enzyme linking and the reaction system is as shown in Table 4.

TABLE 4

| Enzyme linked reaction system | |
|---|---|
| Reagent name | Volume added |
| PMD18-T | 1 µL |
| Reaction product | 4 µL |
| Solution I | 5 µL |

Reaction at 16° C. for 1 h

After the enzyme linking, transform, select clones and conserve the breed, then obtain the anti-human PD-L1 antibody. After sequencing, the nucleic acid sequence and amino acid sequence of heavy chain variable region are obtained and shown as SEQ ID NO: 1 and 2, respectively. The nucleic acid sequence and amino acid sequence of light chain variable region are obtained and shown as SEQ ID NO: 3 and 4, respectively.

2.2 Humanization Design

The screened mouse antibody sequences are analyzed and compared with the human germline genes. The results show that KV1-9*01 is a light chain humanized frame sequence and HV1-46*03 is a heavy chain humanized frame sequence. By CDR-grafting, the CDRs of heavy and light chains are juxtaposed into the framework sequence to construct humanized antibodies and synthesize fragments of humanized antibody variable regions. The nucleic acid sequence and amino acid sequence of heavy chain variable region are obtained and shown as SEQ ID NO: 5 and 6, respectively. The nucleic acid sequence and amino acid sequence of light chain variable region are obtained and shown as SEQ ID NO:7 and 8, respectively.

2.3 Construction of Antibody Library

The DNA sequence of mouse antibody CDR is analyzed to identify the mutation site in variable region CDR. The primer sequence is designed, and the location of the mutation site is designed as NNS to encode any amino acid. By using humanized antibody scFv as template, the scFv antibody library is expanded by PCR. The scFv antibody library is constructed into phage plasmid through sfiI digestion site, so as to build the secondary antibody library.

2.4 Screening of Antibody Library

Afterwards, the high affinity antibodies are screened by phage display, where the specific method is as follows:

A. Transform the phage plasmids of antibody library containing scFv into *Escherichia Coli* TG1 by electroporation. After recovery at 37° C., 220 rpm for 1 h, add the helper phage to the remaining bacteria solution, and add ampicillin. Then cultivate at 37° C., 220 rpm for 1 h. Centrifuge at 2500 rpm×5 min to remove the supernatant, and sowing bacteria with 2×YT-AK medium, then cultivate it at 37° C. and 220 rpm overnight.

B. Envelop antigen: dilute hPD-L1-FC with enveloping buffer, mix it and add it into the immune tube and envelop overnight at 4° C.

C. Collection of recombinant phage: centrifuge the overnight culture medium at 2500 rpm×5 min, collect 10 ml supernatant, add 2 ml PEG/NaCl, mix and place it on ice for 30-60 min. Afterwards, centrifuge for 10000 g×20 min, then remove the supernatant and dissolve the phage library by 2×YT medium.

D. Blocking: wash the immune tube with PBS twice, add the blocking buffer and then place at room temperature for 1 h. In addition, mix the blocking solution with the same volume of phage library to block 10-15 min at room temperature.

E. Incubate phage library: wash the immune tube twice with PBS, add blocked phage library and then incubate it at 37° C. for 2-3 h.

F. Elution: add 100 ml TG1 bacteria solution (inoculated the day before) into 10 ml 2×YT and culture it to A600 value of 0.4-0.5 at 37° C., 220 rpm. Wash the immune tube with PBST for 8 times, then wash with PBS twice, add 5 ml bacteria solution with logarithmic growth phase and then cultivate at 37° C., 220 rpm for 1 h.

G. Output: dilute the bacteria solution to $10^1$ and $10^{-2}$, and apply 100 ul on the plate.

H. Next round of screening: add 200 μl helper phage into 5 ml eluted bacteria solution, then add 5 μl ampicillin into the bacteria solution, and cultivate at 37° C., 220 rpm for 1 h. Centrifuge at 2500 rpm×5 min to remove the supernatant, and sow bacteria with 10 ml 2×YT-AK, then cultivate it at 37° C. and 220 rpm overnight. Repeat steps B-H.

After 3 rounds of screening, select monoclones and prepare recombinant phages. Phage ELISA method is used to detect the activity of recombinant phages. See below for details:

A. Envelop hPD-L1-FC and place at 4° C. overnight;
B. Wash with PBST for twice, add phage supernatant, and cultivate at 25° C. for 1 h;
C. Wash with PBST for three times, add diluted anti-M13-biotinAb, and place at 25° C. for 1 h;
D. Wash with PBST for three times, add diluted HRP-streptavidin, and place at 25° C. for 1 h;
E. Wash with PBST for three times, add preheated TMB and cultivate at 25° C. for 10 min. Add 1M $H_2SO_4$ to stop the reaction, and detect the absorbance by OD450. Select positive clones and send them for sequencing. The heavy or light chain variable region is spliced into the corresponding constant region sequence of human antibody by PCR. The full length fragments of expanded antibody heavy and light chains (including signal peptide) are cloned into pcDNA3.1GS.

Three humanized antibodies, named anti-PD-L1-1, anti-PD-L1-2 and anti-PD-L1-3, are obtained by screening in above experiments. Correspondingly, the heavy-chain and light-chain plasmids of anti-PD-L1-1 are named as P3.1GS-anti-PD-L1-1-HC and P3.1GS-anti-PD-L1-1-LC; the heavy-chain and light-chain plasmids of anti-PD-L1-2 are P3.1GS-anti-PD-L1-2-HC and P3.1GS-anti-PD-L1-2-LC; and the heavy-chain and light-chain plasmids of anti-PD-L1-3 are P3.1GS-anti-PD-L1-3-HC and P3.1GS-anti-PD-L1-3-L. The sequence information is as follows:

Anti-PD-L1-1 heavy chain nucleotide sequence and amino acid sequence are shown in SEQ ID NO: 9 and 10, respectively. Among them, the nucleotide sequence of heavy chain variable region is:

```
                                          (SEQ ID NO: 5)
GAGGTGCAGCTGGTGCAGAGCGGCGCCGAGGTGAAGAAACCTGGCG

CCTCCGTGAAGGTGAGCTGCAAGGCCTCCGGCTACACCTTCACCAAGTAC

ATCATCCACTGGGTGCGGCAAGCCCCTGGACAGGGACTGGAATGGATGGG

CTGGTTCTACCCTGGTTCTGGCAACATCCGGTACAACGAGAAGATCAAGG

GCAGGGTGACCATGACCCGGGACACCAGCACCTCCACCGTGTACATGGAG

CTGTCCTCCCTGAGGAGCGAGGACACCGCCGTGTATTACTGCGCTAGGCA

CGGAGAGCTGGGCGGAGGCTACTTCTTCGACTACTGGGGCCAGGGCACAA

CCGTGACCGTGTCCTCC
```

The underlined parts represent CDR1, CDR2 and CDR3, with serial numbers SEQ ID NO: 11-13, respectively, and the parts with no underline are FR1, FR2, FR3 and FR4 with serial numbers SEQ ID NO:14-17, respectively.

Accordingly, the amino acid sequence of heavy chain variable region is:

```
                                          (SEQ ID NO: 6)
EVQLVQSGAEVKKPGASVKVSCKASGYTFTKYIIHWVRQAPGQGLEW

MGWFYPGSGNIRYNEKIKGRVTMTRDTSTSTVYMELSSLRSEDTAVYYCA

RHGELGGGYFFDYWGQGTTVTSS
```

The underlined parts represent CDR1, CDR2 and CDR3, with serial numbers SEQ ID NO:18-20, respectively, and the parts with no underline are FR1, FR2, FR3 and FR4 with serial numbers SEQ ID NO:21-24, respectively.

Anti-PD-L1-1 light chain nucleotide sequence and amino acid sequence are shown in SEQ ID NO:25 and 26, respectively. Among them, the nucleotide sequence of light chain variable region is:

(SEQ ID NO: 7)
GATATCCAGCTGACCCAGAGCCCCTCCTTTCTGTCCGCCTCCGTGGG

CGACAGGGTGACCATCACCTGC<u>AGGGCCAGCTCCAGCGTGAGCAACATCC</u>

<u>ACTGGTATCAACAGAAGCCTGGCAAGG</u>CCCCCAAGCCCTGGATCTAC<u>GCC</u>

<u>ACCTCCAACCTGGCC</u>AGCGGCGTGCCTAGCAGGTTCAGCGGTTCTGGCTC

CGGCACCGAGTTCACCCTGACCATCTCCTCCCTGCAGCCCGAGGACTTCG

CCACCTACTACTGC<u>CAGCAGTGGTCCAGCAACCCCCTGACC</u>TTTGGCCAG

GGCACCAAGCTGGAGATCAAGAGG

The underlined parts represent CDR1, CDR2 and CDR3, with serial numbers SEQ ID NO:27-29, respectively, and the parts with no underline are FR1, FR2, FR3 and FR4 with serial numbers SEQ ID NO:30-33, respectively.

Accordingly, the amino acid sequence of light chain variable region is:

(SEQ ID NO: 8)
DIQLTQSPSFLSASVGDRVTITC<u>RASSSVSNIH</u>WYQQKPGKAPKPWIY<u>AT</u>

<u>SNLAS</u>GVPSRFSGSGSGTEFTLTISSLQPEDFATYYC<u>QQWSSNPLT</u>FGQG

TKLEIKR

The underlined parts represent CDR1, CDR2 and CDR3, with serial numbers SEQ ID NO: 34-36, respectively, and the parts with no underline are FR1, FR2, FR3 and FR4 with serial numbers SEQ ID NO:37-40, respectively.

2) Anti-PD-L1-2 heavy chain nucleotide sequence and amino acid sequence are shown in SEQ ID NO:9 and 10, respectively. Among them, the nucleotide sequence of heavy chain variable region is:

(SEQ ID NO: 5)
GAGGTGCAGCTGGTGCAGAGCGGCGCCGAGGTGAAGAAACCTGGCGC

CTCCGTGAAGGTGAGCTGCAAGGCCTCCGGCTACACCTTCACC<u>AAGTACA</u>

<u>TCATCCAC</u>TGGGTGCGGCAAGCCCCTGGACAGGGACTGGAATGGATGGGC

<u>TGGTTCTACCCTGGTTCTGGCAACATCCGGTACAACGAGAAGATCAAGGG</u>

CAGGGTGACCATGACCCGGGACACCAGCACCTCCACCGTGTACATGGAGC

TGTCCTCCCTGAGGAGCGAGGACACCGCCGTGTATTACTGCGCTAG<u>GCAC</u>

<u>GGAGAGCTGGGCGGAGGCTACTTCTTCGACTAC</u>TGGGGCCAGGGCACAAC

CGTGACCGTGTCCTCC

The underlined parts represent CDR1, CDR2 and CDR3, with serial numbers SEQ ID NO:11-13, respectively, and the parts with no underline are FR1, FR2, FR3 and FR4 with serial numbers SEQ ID NO:14-17, respectively.

Accordingly, the amino acid sequence of heavy chain variable region is:

(SEQ ID NO: 6)
EVQLVQSGAEVKKPGASVKVSCKASGYTFT<u>KYIIH</u>WVRQAPGQGLEW

MG<u>WFYPGSGNIRYNEKIK</u>GRVTMTRDTSTSTVYMELSSLRSEDTAVYYCA

R<u>HGELGGGYFFDY</u>WGQGTTVTVSS

The underlined parts represent CDR1, CDR2 and CDR3, with serial numbers SEQ ID NO: 18-20, respectively, and the parts with no underline are FR1, FR2, FR3 and FR4 with serial numbers SEQ ID NO: 21-24, respectively.

Anti-PD-L1-2 light chain nucleotide sequence and amino acid sequence are shown in SEQ ID NO: 41 and 42, respectively. Among them, the nucleotide sequence of light chain variable region is:

(SEQ ID NO: 43)
GATATCCAGCTGACCCAGAGCCCCTCCTTTCTGTCCGCCTCCGTGGG

CGACAGGGTGACCATCACCTGC<u>AGGGCCAGCTCCAAGACGGGGAACATC</u>

<u>CACTGGTATCAACAGAAGCCTGGCAAGG</u>CCCCCAAGCCCTGGATCTAC<u>G</u>

<u>CCACCTCCAACCTGGCCAGC</u>GGCGTGCCTAGCAGGTTCAGCGGTTCTGG

CTCCGGCACCGAGTTCACCCTGACCATCTCCTCCCTGCAGCCCGAGGAC

TTCGCCTACTACTGC<u>CAGCAGTGGTCCAGCAACCCCCTGACC</u>TTTGGCC

AGGGCACCAAGCTGGAGATCAAGAGG

The underlined parts represent CDR1, CDR2 and CDR3, with serial numbers SEQ ID NO: 44, 28, 29, respectively, and the parts with no underline are FR1, FR2, FR3 and FR4 with serial numbers SEQ ID NO: 30-33, respectively.

Accordingly, the amino acid sequence of light chain variable region is:

(SEQ ID NO: 45)
DIQLTQSPSFLSASVGDRVTITC<u>RASSKTGNIH</u>WYQQKPGKAPKPWIY<u>AT</u>

<u>SNLAS</u>GVPSRFSGSGSGTEFTLTISSLQPEDFATYYC<u>QQWSSNPLT</u>FGQGT

KLEIKR

The underlined parts represent CDR1, CDR2 and CDR3, with serial numbers SEQ ID NO: 46, 35, 36, respectively, and the parts with no underline are FR1, FR2, FR3 and FR4 with serial numbers SEQ ID NO: 37-40, respectively.

3) Anti-PD-L1-3 heavy chain nucleotide sequence and amino acid sequence are shown in SEQ ID NO:9 and 10, respectively. Among them, the nucleotide sequence of heavy chain variable region is:

(SEQ ID NO: 5)
GAGGTGCAGCTGGTGCAGAGCGGCGCCGAGGTGAAGAAACCTGGCG

CCTCCGTGAAGGTGAGCTGCAAGGCCTCCGGCTACACCTTCACC<u>AAGTA</u>

<u>CATCATCCAC</u>TGGGTGCGGCAAGCCCCTGGACAGGGACTGGAATGGATG

GGC<u>TGGTTCTACCCTGGTTCTGGCAACATCCGGTACAACGAGAAGATCA</u>

<u>AGGGC</u>AGGGTGACCATGACCCGGGACACCAGCACCTCCACCGTGTACAT

GGAGCTGTCCTCCCTGAGGAGCGAGGACACCGCCGTGTATTACTGCGCT

AGG<u>CACGGAGAGCTGGGCGGAGGCTACTTCTTCGACTAC</u>TGGGGCCAGG

GCACAACCGTGACCGTGTCCTCC

The underlined parts represent CDR1, CDR2 and CDR3, with serial numbers SEQ ID NO: 11-13, respectively, and the parts with no underline are FR1, FR2, FR3 and FR4 with serial numbers SEQ ID NO: 14-17, respectively.

Accordingly, the amino acid sequence of heavy chain variable region is:

(SEQ ID NO: 6)
EVQLVQSGAEVKKPGASVKVSCKASGYTFT<u>KYIIH</u>WVRQAPGQGLEW

MG<u>WFYPGSGNIRYNEKIK</u>GRVTMTRDTSTSTVYMELSSLRSEDTAVYYCA

R<u>HGELGGGYFFDY</u>WGQGTTVTVSS

The underlined parts represent CDR1, CDR2 and CDR3, with serial numbers SEQ ID NO: 18-20, respectively, and the parts with no underline are FR1, FR2, FR3 and FR4 with serial numbers SEQ ID NO: 21-24, respectively.

Anti-PD-L1-3 light chain nucleotide sequence and amino acid sequence are shown in SEQ ID NO: 47 and 48, respectively. Among them, the nucleotide sequence of light chain variable region is:

(SEQ ID NO: 49)
GATATCCAGCTGACCCAGAGCCCCTCCTTTCTGTCCGCCTCCGTGGG

CGACAGGGTGACCATCACCTGC<u>AGGGCCAGCTCCGGCGCGTCCAACATC</u>

<u>CACTGGTATCAACAGAAGCCTGGCAAGGCCCCCAAGCCCTGGATCTACG</u>

<u>CCACCTCCAACCTGGCCAGC</u>GGCGTGCCTAGCAGGTTCAGCGGTTCTGG

CTCCGGCACCGAGTTCACCCTGACCATCTCCTCCCTGCAGCCCGAGGAC

TTCGCCACCTACTACTGC<u>CAGCAGTGGTCCAGCAACCCCCTGACC</u>TTTG

GCCAGGGCACCAAGCTGGAGATCAAGAGG

The underlined parts represent CDR1, CDR2 and CDR3, with serial numbers SEQ ID NO: 50, 28, 29, respectively, and the parts with no underline are FR1, FR2, FR3 and FR4 with serial numbers SEQ ID NO: 30-33, respectively.

Accordingly, the amino acid sequence of light chain variable region is:

(SEQ ID NO: 51)
DIQLTQSPSFLSASVGDRVTITC<u>RASSGASNIH</u>WYQQKPGKAPKPWIY<u>AT</u>

<u>SNLAS</u>GVPSRFSGSGSGTEFTLTISSLQPEDFATYYC<u>QQWSSNPLT</u>FGQG

TKLEIKR

The underlined parts represent CDR1, CDR2 and CDR3, with serial numbers SEQ ID NO: 52, 35, 36, respectively, and the parts with no underline are FR1, FR2, FR3 and FR4 with serial numbers SEQ ID NO: 37-40, respectively.

Embodiment 3: Construction of Humanized Antibody Expression Plasmid

Because all the three antibodies expressed well specificity, this embodiment only uses P3.1GS-PD-L1-1-HC and P3.1GS-PD-L1-1-LC as templates for further explanation. The heavy and light chain fragments of full-length antibody are expanded by PCR to construct humanized antibody expression plasmid.

The upstream and downstream primers for light and heavy chains, reaction systems and PCR conditions are shown in Table 5, table 6 and table 7, respectively.

TABLE 5

Upstream and downstream primers of PCR reaction for light and heavy chain of humanized antibody

| Primer | Sequence |
| --- | --- |
| Heavy chain upstream | 5'GGGGTACCGCCGCCACCATGGAGACAGACACACTCCTGCT ATGGGTACTGCTGCTCTGGGTTCCAGGTTCCACTGGTGAGG TGCAGCTGGTGCAGAG 3' (SEQ ID NO: 53) |
| Heavy chain downstream | 5'GGCTCTAGATTATCACTTTCCAGGGGACAGTGAC 3' (SEQ ID NO: 54) |
| Light chain upstream | 5'GGGGTACCGCCGCCACCATGGAGACAGACACACTCCTGCT ATGGGTACTGCTGCTCTGGGTTCCAGGTTCCACTGGTGATAT CCAGCTGACCCAGAG 3' (SEQ ID NO: 55) |
| Lightchain downstream | 5'GGCTCTAGATTAACACTCTCCCCTGTTGAAGC 3' (SEQ ID NO: 56) |

TABLE 6

PCR reaction system for light and heavy chain of humanized antibody

| Reagent name | Volume added |
| --- | --- |
| Heavy/light chain template | 1 μL |
| 5×Buffer | 10 μL |
| 2.5 μM dNTP Mix | 4 μL |
| Upstream and downstream primers (10 μM) | 1 μL for each |
| Taq | 0.5 μL |
| ddH$_2$O | up to 50 μL |

TABLE 7

PCR reaction conditions for light and heavy chain of humanized antibody

| Temperature | Time | |
| --- | --- | --- |
| 94° C. | 5 min | |
| 94° C. | 30 s | Totally 30 cycles |
| 50° C. | 30 s | |
| 72° C. | 1 min 45 s | |
| 72° C. | 7 min | |

Cool to 4° C.

The full-length sequences of light and heavy chains are recovered by PCR product recovery kit. The light chain, heavy chain and plasmid of the antibody fragment are digested by double enzyme digestion. The antibody and plasmid enzyme digestion fragments after electrophoresis are recovered by gel digestion, then linked by enzyme. The humanized antibody expression plasmid after enzyme linking is named as P3.1GS-PD-L1-1. The reaction systems are as shown in Tables 8-10.

TABLE 8

Double enzyme digestion reaction systems for light chain and heavy chain of humanized antibody

| Reagent name | Volume added |
|---|---|
| Fragment | 22 μL |
| Buffer | 3 μL |
| Kpnl | 1.5 μL |
| Xba 1 | 1.5 μL |
| ddH$_2$O | Up to 30 μL |

37° C. water bath overnight

TABLE 9

Double enzyme digestion reaction system of expression plasmid

| Reagent name | Volume added |
|---|---|
| Plasmid pcDNA3.1GS | 1 μL |
| Buffer | 2 μL |
| Kpnl | 1 μL |
| Xba 1 | 1 μL |
| ddH$_2$O | Up to 20 μL |

37° C. water bath overnight

TABLE 10

Enzyme linked reaction system of antibody fragments and expression plasmid fragments

| Reagent name | Volume added |
|---|---|
| Plasmid fragment | 1 μL |
| Light chain/heavy chain fragment | 4 μL |
| Solution I | 5 μL |

Reaction at 16° C. for 1 h

Adding the enzyme linking product to 100 μL XL1-10 competent cells and place it on ice for 30 minutes. Then heat it at 42° C. for 90 seconds, and place it on ice rapidly for 2 minutes. Next add 500 μL LB medium, culture at 37° C. for 1 hour in shaker, centrifuge at 4000 rpm for 5 minutes and remove 500 μL supernatant, and then spray on LB solid plate containing 50 μg/mL AMP by gun blowing the suspension, and culture at 37° C. overnight. Add single colonies into 5 mL LB liquid medium (50μg/mL AMP) and culture for 6 hours at 37° C., 250 rpm. Verify the clones by PCR, and preserve the positive strains with 15% sterilized glycerol. Each clone is prepared with 2 copies, one stored in a tube for sequencing, and the other preserved at −20° C.

Embodiment 4: Construction of Stable Expression Cell Lines

The humanized antibody expression plasmid P3.1GS-PD-L1-1 is linearized by PvuI before transfection, and the linearized plasmid containing humanized antibody light and heavy chain genes is transfected into CHO-KSM4 by electrotransfection for 2 times.

After transfection, glutamine is withdrawn for pressurized screening, and the transfected cells are recovered for 2 days and then laid on the plate. After culturing for 30-40 days, growth of clones can be observed in the 96-well plate, when the yield is verified. High-yield clones are transferred and expanded for culturing. When the quantity of cells reaches about 2×10$^6$ cells/mL, they are inoculated, fed and cultured in batches. After culturing, the supernatant is harvested for yield verification, to obtain the alternative parent clones. Carry out subclonal screening on the high-yield clones: 3000-5000 cells per well are arranged on a 6-well plate through semisolid plating, with 2.5 mL medium. After plating, place at 37° C. and 5% CO2 for static culture 7-12 days, after which select monoclonal clones. The selected clones are verified for yield to obtain alternative clones.

Nine high yield cell lines are obtained for flask shaking & feeding experiment. The feeding scheme by flask shaking is as follows: CDM4CHO-based medium is used to inoculate, with the density of inoculation of 5×10$^5$ cells/mL, and the inoculated cells are cultured at 37° C., 5% CO2 and 120 rpm. The day starting the inoculation is marked as Day 0. And 70 g/L cell Boost 5 is supplemented on Day 3. The supplemented volume per day is 6% of the inoculation volume until the cells are harvested. After feeding, the highest yield of cell lines reaches 1.97 g/L, and the antibody expressed is named as anti-PD-L1-1.

Figure 5:
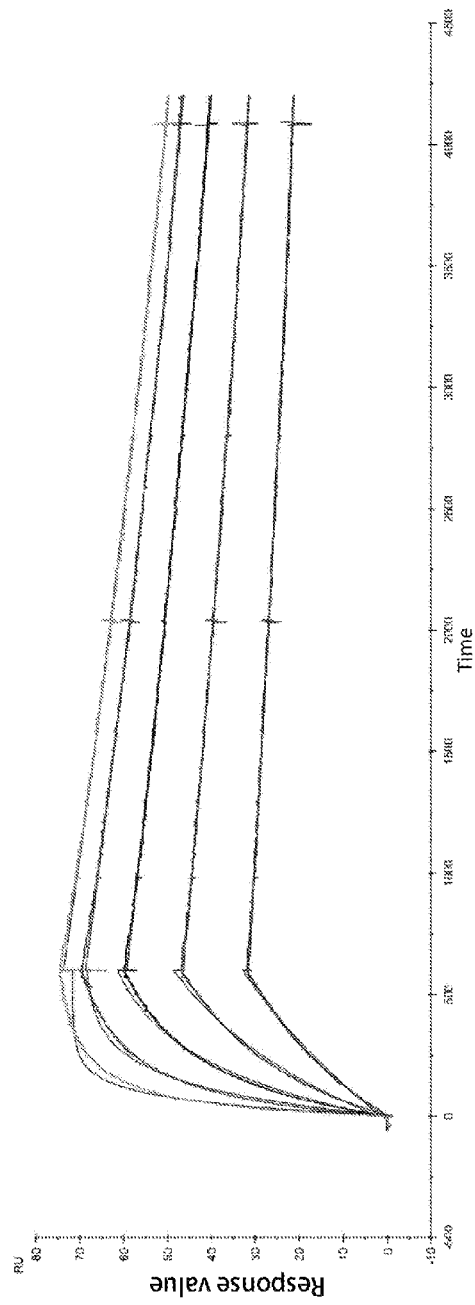
FIG. 5 shows the binding kinetics curve of humanized PD-L1 antibody.

Embodiment 5: Comparison of Binding Specificity and Binding Kinetics of Antibodies Biacore is used to analyze the affinity and binding kinetics of the antibody expressed in cell line 4. Using standard amine coupling chemistry and the kit provided by Biacore, the goat anti-human IgG is covalently linked to CM5 chip by primary amine. Make the antibody flow in the HBS EP buffer at a flow rate of 10 L/min and measure the binding. The binding time is 300 seconds, and the dissociation time is 1200 seconds. The measured binding kinetics curve is as shown in FIG. 5, and the measured values ka, kd and KD are given in Table 11.

TABLE 11

Binding kinetics results of humanized antibody anti-PD-L1-1

| Sample | ka (1/Ms) | kd (1/s) | KD (M) |
|---|---|---|---|
| anti-PD-L1-1 | $1.76 \times 10^5$ | $1.72 \times 10^{-4}$ | $4.06 \times 10^{-10}$ |

Embodiment 6: ELISA Assay and its Binding Specificity to Other Members of B7 Family and Binding to PD-L1 Proteins of Different Species The binding of B7 family members B7-1, B7-2 to PD-L2 protein, and the binding of mouse, *M. fascicularis* and human PD-L1 protein to humanized antibody anti-PD-L1-1 are tested. Different proteins are stored at 0.5 g/mL in enveloping buffer at 4° C. overnight. Remove the solution in wells the next day and wash with PBST for twice. Then add 1% BSA, seal at 37° C. for 1 hour, then wash with PBST for twice. Add 0.5 μg/mL antibody samples, incubate for 1 hour, and wash with PBST for three times. Dilute with goat anti-human FAB-HRP at ratio of 1:10000, incubate for 1 hour at 37 C, and wash with PBST for three times. Add TMB for 15 min coloration, stop the reaction with 0.5M H$_2$SO$_4$ and read out the absorbance at 450 nm.

Figure 6:
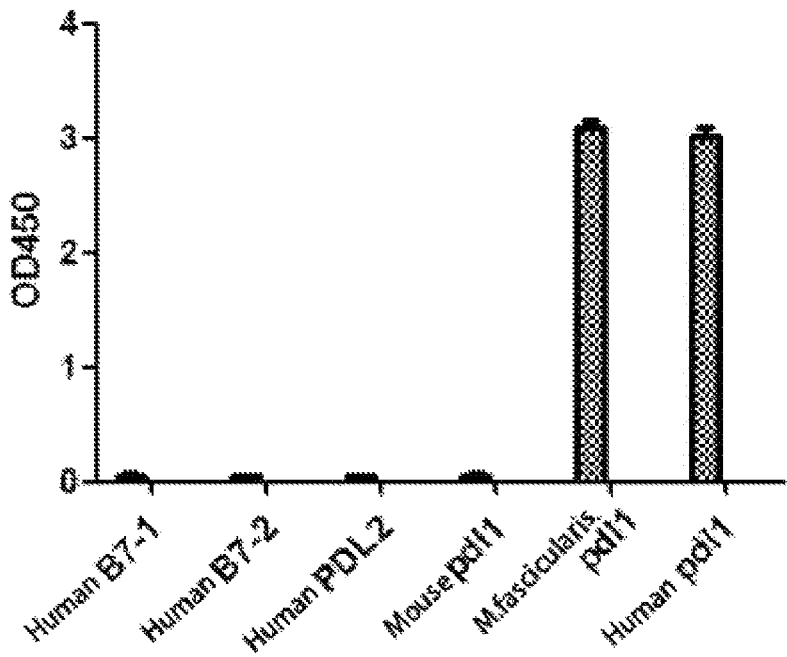
FIG. 6 shows the result of the binding specificity of humanized PD-L1 antibody to other B7 family members and the binding to PD-L1 protein of different species.

As shown in FIG. 6, humanized antibody anti-PD-L1-1 does not bind to other members of B7 family. Humanized antibody anti-PD-L1-1 binds to human or *M. fascicularis* PD-L1 protein with similar affinity.

Embodiment 7 ELISA Assay for Binding Specificity of Antibodies to CHO Cells with PD-L1 Expressed on Surface A Chinese hamster ovary (CHO) cell line expressing recombinant human PD-L1 on cell surface is constructed and its binding specificity to humanized antibody anti-PD-L1-1 is determined by ELISA assay. The cells are overlaid on PD-L1 the day before the test, and $\frac{1}{200}$ cells are filled with T75 bottles on each well. Then add 1% BSA and seal at 37° C. for 1 hour. The antibody is diluted three folds starting from 5 μg/mL for 8 concentration gradients, incubated at 25° C. for 1 hour, and washed with PBST for one time. The volume of 50 ng/mL anti-human-Eu added to each well is 100 μL, with reaction time of 0.5 hours at 25° C., and washing with PBS for one time. Add fluorescence enhancement liquid and read values at exciting light 337 nm/emitted light 620 nm.

Figure 7:
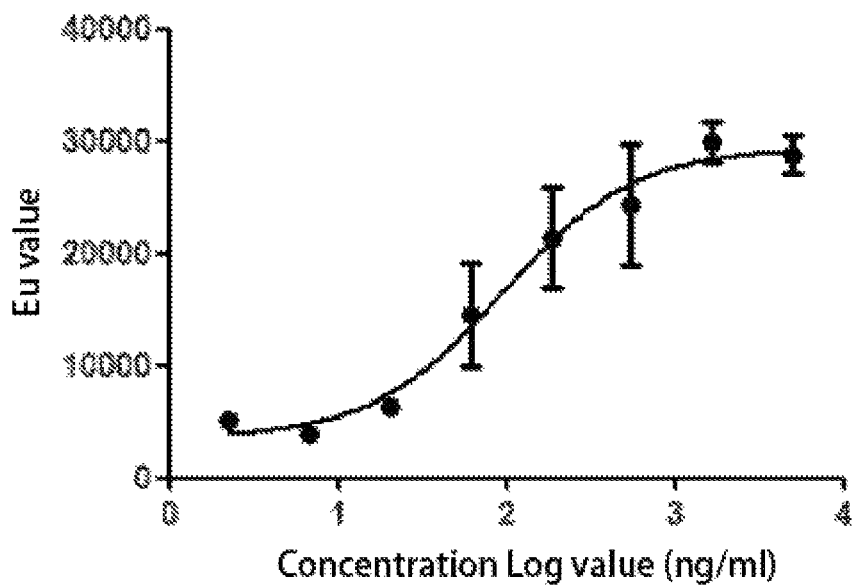
FIG. 7 shows the result of the binding specificity of humanized PD-L1 antibody to CHO cells with PD-L1 expressed on the surface.

As shown in FIG. 7, the humanized antibody anti-PD-L1-1 can effectively bind to the CHO cells transfected by PD-L1, and the EC50 reaches 93.50 ng/mL.

Embodiment 8 ELISA Assay for Binding Specificity of Antibodies to Recombinant Human PD-L1 Fusion Protein The recombinant human PD-L1 fusion protein of 0.5 μg/mL is stored at 4° C. overnight in enveloping buffer. Remove the solution in wells the next day and wash with PBST for twice. Then add 1% BSA and seal at 37° C. for 1 hour. Wash with PBST for twice. The antibody is diluted three folds starting from 5 μg/mL for 8 concentration gradients, incubated at 25° C. for 1 hour, and washed with PBST for three time. Dilute with goat anti-human FAB-HRP at ratio of 1:10000, incubate for 1 hour at 37 C, and wash with PBST for three times. Add TMB for 15 min coloration, stop the reaction with 0.5M $H_2SO_4$ and read out the absorbance at 450 nm.

Figure 8:
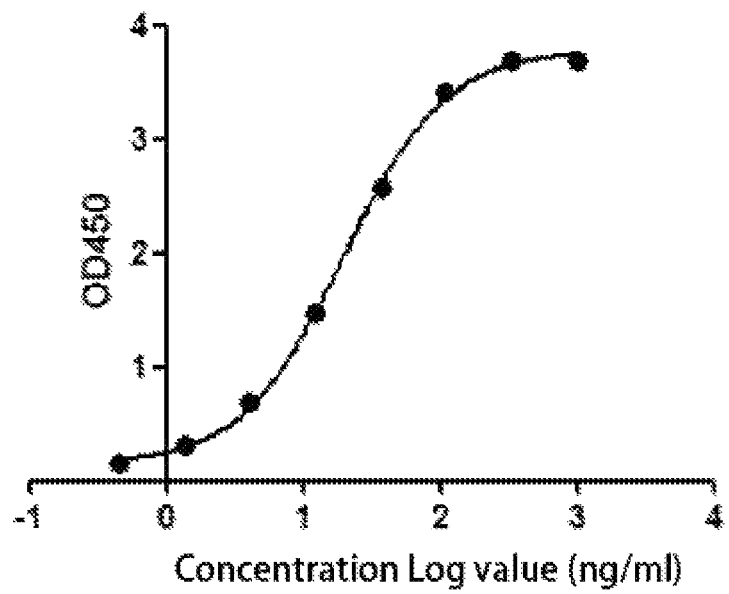
FIG. 8 shows the result of the binding specificity of humanized PD-L1 antibody to recombinant human PD-L1 fusion protein.

As shown in FIG. 8, the humanized antibody anti-PD-L1-1 can effectively interact with the recombinant human PD-L1 fusion protein, and the EC50 is 19.47 ng/mL.

Embodiment 8 Blocking Effect of Antibody on PD-L1 Binding to PD-1

The recombinant human PD-L1 fusion protein of 0.5 μg/mL is stored at 4° C. overnight in enveloping buffer. Remove the solution in wells the next day and wash with PBST for twice. Then add 1% BSA, seal at 37° C. for 1 hour, then wash with PBST for twice. The antibody is diluted 2.5 folds starting from 10 μg/mL for 8 concentration gradients, mixed with same volume of 1 μg/mL PD1-Fc-Biotin, incubated at 25° C. for 1 hour, and washed with PBST for one time. Incubate with goat streptavidin-HRP at ratio of 1:10000 for 1 hour at 37 C, and wash with PBST for three times. Add TMB for 15 min coloration, stop the reaction with 0.5M $H_2SO_4$ and read out the absorbance at 450 nm.

Figure 9:
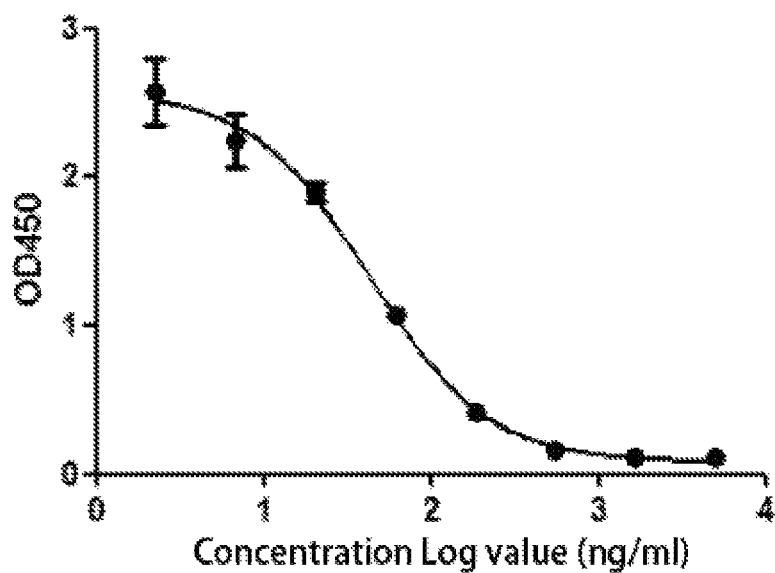
FIG. 9 shows the result of the blocking effect of humanized PD-L1 antibody on PD-L1 binding to PD-1.

As shown in FIG. 9, the humanized antibody anti-PD-L1-1 can block the binding of ligands PD-L1 to PD-1, and the IC50 is 43.16 ng/mL.

Embodiment 10: Antibody Effect on Cytokine Secretion in Mixed Lymphocyte Reaction Dilute the blood with PBS buffer at 1:1, move 3 mL LSM into the centrifugal tube, and add 4 mL diluted blood. When adding, ensure that the diluted blood to the upper layer of LSM, without mixing. RT centrifuge at 400 g for 30-40 min. Finally, extract the separated PBMC from the upper layer and centrifuge at 100 g for 10 min. Separate CD4+ T-cells by using BD's CD4+ cell separation magnetic beads, and separate DC cells by using BD's DC-cell separation magnetic beads. On the 96-well plate, the quantity of CD4+T-cells is $1 \times 10^5$ per well; the quantity of DC is $1 \times 10^4$; and the total volume is 100 μL for co-culture. Add gradient-diluted antibody and culture for 5 days so as to test the concentrations of IFN-γ, IL-2.

Figure 10:
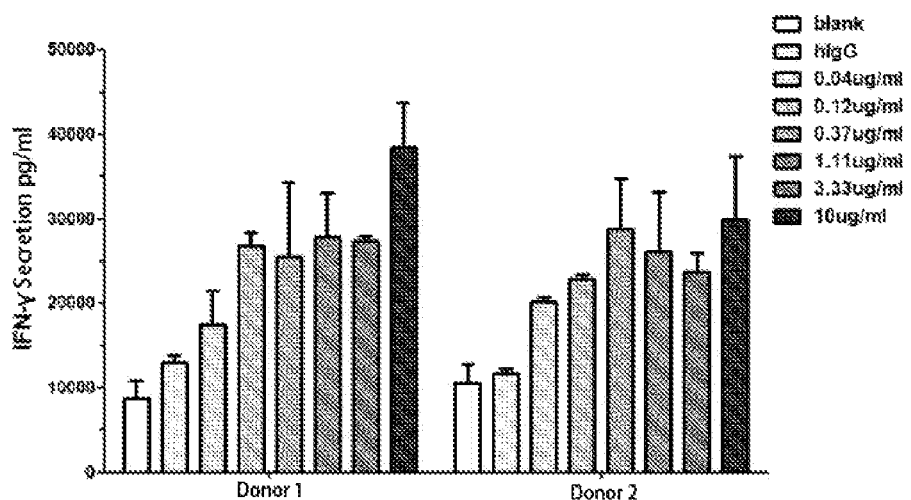
FIG. 10 shows the result of the effect of humanized PD-L1 antibody on cytokine IFN-γ secretion in mixed lymphocyte reaction.
Figure 11:
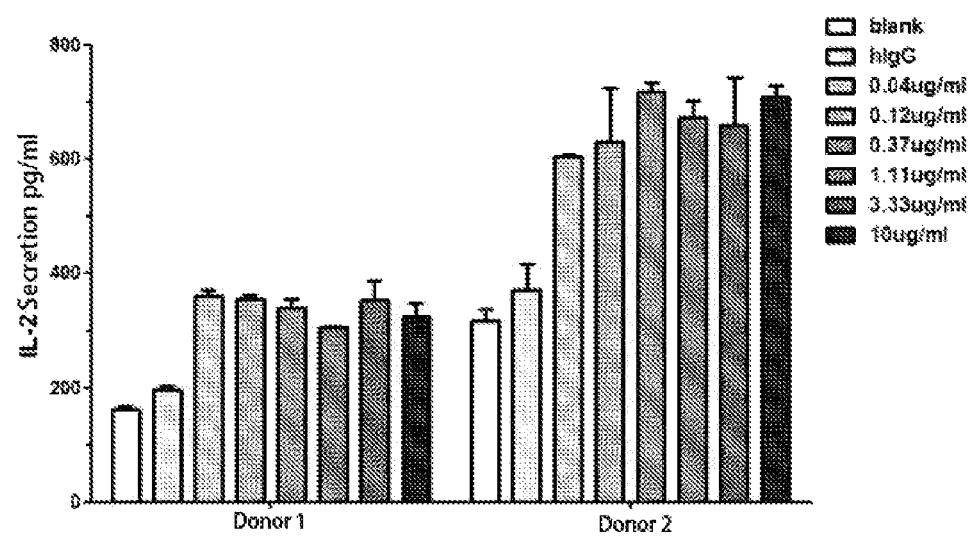
FIG. 11 shows the result of the effect of humanized PD-L1 antibody on cytokine IL-2 secretion in mixed lymphocyte reaction.

As shown in FIGS. 10 and 11, the humanized antibody anti-PD-L1-1 can effectively promote the secretion of IFN-γ and IL-2 by mixed lymphocytes.

Embodiment 11: Stability of Antibody in Serum

Dilute the humanized antibody anti-PD-L1-1 with monkey serum, at a concentration of 0.5 mg/mL. Place it at 37° C., for 0, 1, 4 and 7 days, respectively.

Figure 12:
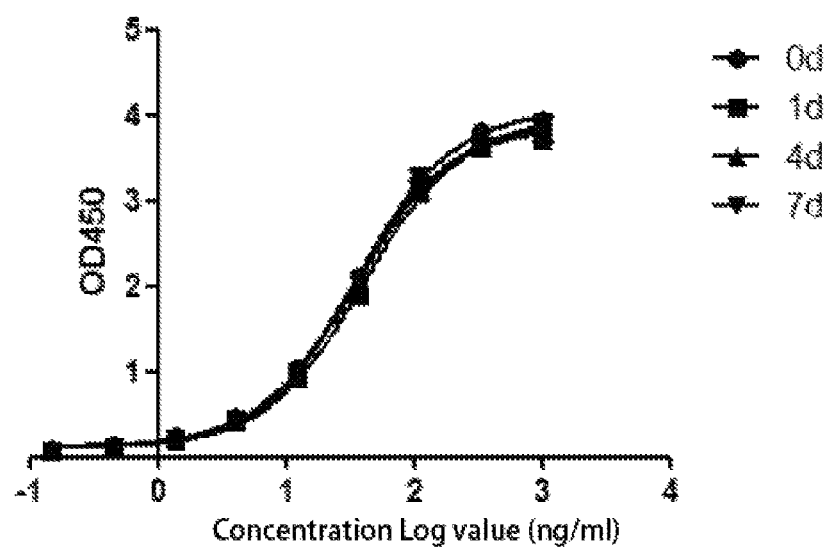
FIG. 12 shows the stability result of humanized PD-L1 antibody in serum.

The recombinant human PD-L1 fusion protein is stored at the concentration of 0.5 μg/mL at 4° C. overnight in enveloping buffer. Remove the solution in wells the next day and wash with PBST for twice. Then add 1% BSA, seal at 37° C. for 1 hour, then wash with PBST for twice. The stable antibody samples are diluted three folds starting from 1 μg/mL for 8 concentration gradients, incubated at 37° C. for 1 hour, and washed with PBST for three times. Dilute with goat anti-human FAB-HRP at ratio of 1:10000, incubate for 1 hour at 37 C, and wash with PBST for three times. Add TMB for 15 min coloration, stop the reaction with 0.5M $H_2SO_4$ and read out the absorbance at 450 nm. With results as shown in FIG. 12, the humanized antibody anti-PD-L1-1 shows good serum stability, without significant activity attenuation within 7 days.

The preceding is simply a preferred embodiment of the present invention and is not intended to limit the invention. It should be pointed out that, for those with ordinary skills in the art, a number of improvements and variations can be made without departing from the technical principles of the invention, and these improvements and variations should also be regarded as being in the protection scope of the invention.

What is claimed is:

1. A humanized monoclonal antibody or an antigen-binding part thereof that binds to human PD-L1, wherein the humanized monoclonal antibody or antigen-binding part thereof comprises:
- (1) a heavy chain with three CDRs comprising
    - a CDR1 comprising amino acid sequence SEQ ID NO: 18,
    - a CDR2 comprising amino acid sequence SEQ ID NO: 19, and
    - a CDR3 comprising amino acid sequence SEQ ID NO: 20; and
    - a light chain with three CDRs comprising
    - a CDR1 comprising amino acid sequence SEQ ID NO: 34,
    - a CDR2 comprising amino acid sequence SEQ ID NO: 35, and
    - a CDR3 comprising amino acid sequence SEQ ID NO: 36; or
- (2) a heavy chain with three CDRs comprising
    - a CDR1 comprising amino acid sequence SEQ ID NO: 18,
    - a CDR2 comprising amino acid sequence SEQ ID NO: 19, and
    - a CDR3 comprising amino acid sequence SEQ ID NO: 20; and
    - a light chain with three CDRs comprising
    - a CDR1 comprising amino acid sequence SEQ ID NO: 46,
    - a CDR2 comprising amino acid sequence SEQ ID NO: 35, and
    - a CDR3 comprising amino acid sequence SEQ ID NO: 36; or
- (3) a heavy chain with three CDRs comprising
    - a CDR1 comprising amino acid sequence SEQ ID NO: 18,
    - a CDR2 comprising amino acid sequence SEQ ID NO: 19, and
    - a CDR3 comprising amino acid sequence SEQ ID NO: 20; and
    - a light chain with three CDRs comprising
    - a CDR1 comprising amino acid sequence SEQ ID NO: 52,
    - a CDR2 comprising amino acid sequence SEQ ID NO: 35, and
    - a CDR3 comprising amino acid sequence SEQ ID NO: 36.

2. The humanized monoclonal antibody or antigen-binding part thereof of claim 1, wherein framework regions of the heavy chain variable region FR1, FR2, FR3 and FR4 comprise amino acid sequences which are at least 70%, 80%, 85%, 90%, 95%, or 99% identical to SEQ ID NO: 21, 22, 23 and 24, respectively.

3. The humanized monoclonal antibody or antigen-binding part thereof of claim 2, wherein the heavy chain comprises amino acid sequence SEQ ID NO: 10.

4. The humanized monoclonal antibody or antigen-binding part thereof of claim 1, wherein framework regions of the light chain variable region FR1, FR2, FR3 and FR4 comprise amino acid sequences which are at least 70%, 80%, 85%, 90%, 95%, or 99% identical to SEQ ID NO: 37, 38, 39 and 40, respectively.

5. The humanized monoclonal antibody or antigen-binding part thereof of claim 4, wherein the light chain comprises amino acid sequence SEQ ID NO: 26.

6. A nucleic acid molecule encoding the humanized monoclonal antibody or antigen-binding part thereof of claim 1.

7. The nucleic acid molecule of claim 6, wherein the heavy chain variable region of the humanized monoclonal antibody or antigen-binding part thereof comprises amino acid sequence SEQ ID NO: 6.

8. The nucleic acid molecule of claim 6, wherein the light chain variable region of the humanized monoclonal antibody or antigen-binding part thereof comprises amino acid sequence SEQ ID NO: 8.

9. A carrier comprising the nucleic acid molecule of claim 6.

10. A host cell comprising the nucleic acid molecule of claim 6.

11. A conjugate comprising the humanized monoclonal antibody or antigen-binding part thereof of claim 1 and a bioactive substance, wherein the bioactive substance is coupled to the humanized monoclonal antibody or antigen-binding part thereof directly or through a junction fragment.

12. A composition comprising the humanized monoclonal antibody or antigen-binding part thereof of claim 1, and pharmaceutically acceptable carriers or excipients.

13. A composition comprising: the nucleic acid molecule of claim 6, a carrier comprising the nucleic acid molecule of claim 6, or a host cell comprising the nucleic acid molecule of claim 6, and optionally further comprising pharmaceutically acceptable carriers or excipients.

14. A composition comprising the conjugate of claim 11, and optionally further comprising pharmaceutically acceptable carriers or excipients.

* * * * *